United States Patent
Wubbels et al.

(10) Patent No.: US 11,580,422 B1
(45) Date of Patent: Feb. 14, 2023

(54) VALIDATING A MACHINE LEARNING MODEL AFTER DEPLOYMENT

(71) Applicant: Google LLC, Mountain View, CA (US)

(72) Inventors: Peter Wubbels, Redwood City, CA (US); Tyler Rhodes, San Francisco, CA (US); Jin Zhang, San Jose, CA (US); Kira Whitehouse, Palo Alto, CA (US); Rohan Ganeshananthan, San Francisco, CA (US)

(73) Assignee: GOOGLE LLC, Mountain View, CA (US)

( * ) Notice: Subject to any disclaimer, the term of this patent is extended or adjusted under 35 U.S.C. 154(b) by 330 days.

(21) Appl. No.: 16/818,804

(22) Filed: Mar. 13, 2020

Related U.S. Application Data

(63) Continuation of application No. 15/926,479, filed on Mar. 20, 2018, now Pat. No. 10,599,984.

(51) Int. Cl.
| | |
|---|---|
| G06N 5/04 | (2006.01) |
| G16H 30/40 | (2018.01) |
| G16H 50/20 | (2018.01) |
| G06N 20/00 | (2019.01) |

(52) U.S. Cl.
CPC ........... *G06N 5/04* (2013.01); *G06N 20/00* (2019.01); *G16H 30/40* (2018.01); *G16H 50/20* (2018.01)

(58) Field of Classification Search
CPC ........ G06N 5/022; G06N 5/04; G06N 99/005; G16H 50/20; G16H 30/40
See application file for complete search history.

(56) References Cited

U.S. PATENT DOCUMENTS

| | | | |
|---|---|---|---|
| 9,165,051 B2 | 10/2015 | Masud et al. | |
| 10,140,421 B1 * | 11/2018 | Bernard | G06N 3/04 |
| 10,599,984 B1 * | 3/2020 | Wubbels | G16H 50/20 |
| 2012/0155725 A1 | 6/2012 | Bathe et al. | |
| 2014/0233826 A1 | 8/2014 | Agaian et al. | |
| 2016/0321414 A1 * | 11/2016 | Salganicoff | G06N 20/00 |
| 2017/0132528 A1 | 5/2017 | Aslan et al. | |
| 2018/0082002 A1 | 3/2018 | Demena et al. | |
| 2019/0034830 A1 * | 1/2019 | Burangulov | G06F 16/953 |

OTHER PUBLICATIONS

Fraz, Muhammad M. et al., "An Ensemble Classification-Based Approach Applied to Retinal Blood Vessel Segmentation", IEEE Transactions on Biomedical Engineering, vol. 59, No. 9, pp. 2538-2548; Sep. 2012, Sep. 2012, pp. 2538-2548.

(Continued)

*Primary Examiner* — Ying Yu Chen
(74) *Attorney, Agent, or Firm* — Dority & Manning, P.A.

(57) ABSTRACT

Machine learning models used in medical diagnosis should be validated after being deployed in order to reduce the number of misdiagnoses. Validation processes presented here assess a performance of the machine learning model post-deployment. In post-deployment validation, the validation process monitoring can include: (1) monitoring to ensure a model performs as well as a reference member such as another machine learning model, and (2) monitoring to detect anomalies in data. This post-deployment validation helps identify low-performing models that are already deployed, so that relevant parties can quickly take action to improve either the machine learning model or the input data.

20 Claims, 16 Drawing Sheets

(56) References Cited

OTHER PUBLICATIONS

Kolter, J. Zico et al., "Dynamic Weighted Majority: An Ensemble Method for Drifting Concepts", Journal of Machine Learning Research 8; pp. 2755-2790; (Year: 2007), Dec. 2007, 2755-2790.

Lee, Ryong et al., "Measuring Geographical Regularities of Crowd Behaviors for Twitter-based Geo-social Event Detection", ACM LBSN'10, pp. 1-10, Nov. 2, 2010,, Nov. 2, 2010, pp. 1-10.

Muhlbaier, Michael D. et al., "Learn++.NC: Combining Ensemble of Classifiers With Dynamically Weighted Consult-and-Vote for Efficient Incremental Learning of New Classes", Dec. 22, 2008, IEEE Transactions on Neural Networks, vol. 20, No. 1 ,pp. 152-168. (Year: 2008), Dec. 22, 2008, 152-168.

Zhou, Xiangrong et al., "Three-Dimensional CT Image Segmentation by Combining 2D Fully Convolutional Network with 3D Majority Voting", Springer International Publishing AG, pp. 1-10., Jan. 10, 2016.

\* cited by examiner

VALIDATING A MACHINE LEARNING MODEL AFTER DEPLOYMENT

CROSS REFERENCE TO RELATED APPLICATION

This application is a continuation of U.S. patent application Ser. No. 15/926,479, titled "VALIDATING A MACHINE LEARNING MODEL AFTER DEPLOYMENT," filed on Mar. 20, 2018, which is incorporated by reference herein in its entirety.

TECHNICAL FIELD

Various embodiments concern techniques for validating a machine learning model used in a medical device.

BACKGROUND

Medical imaging is a technique for creating visual representations of a subject's body for clinical analysis and medical intervention, as well as visual representation of the function of some organs or tissues. Medical imaging can reveal hidden internal structures and can be used to diagnose and treat a disease.

Various medical imaging techniques exist including fundus photography. Fundus photography involves capturing a photograph of the back of a subject's eye. A fundus photo can include visual representations of a central and peripheral retina, optic disc, and macula that vary widely among subjects. A misdiagnosis of medical imagery by an automated technique is no different than a misdiagnosis made by a trained doctor—it can harm patients and undermine public trust.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. While the accompanying drawings include illustrations of various embodiments, the drawings are not intended to limit the claimed subject matter.

Figure 1:
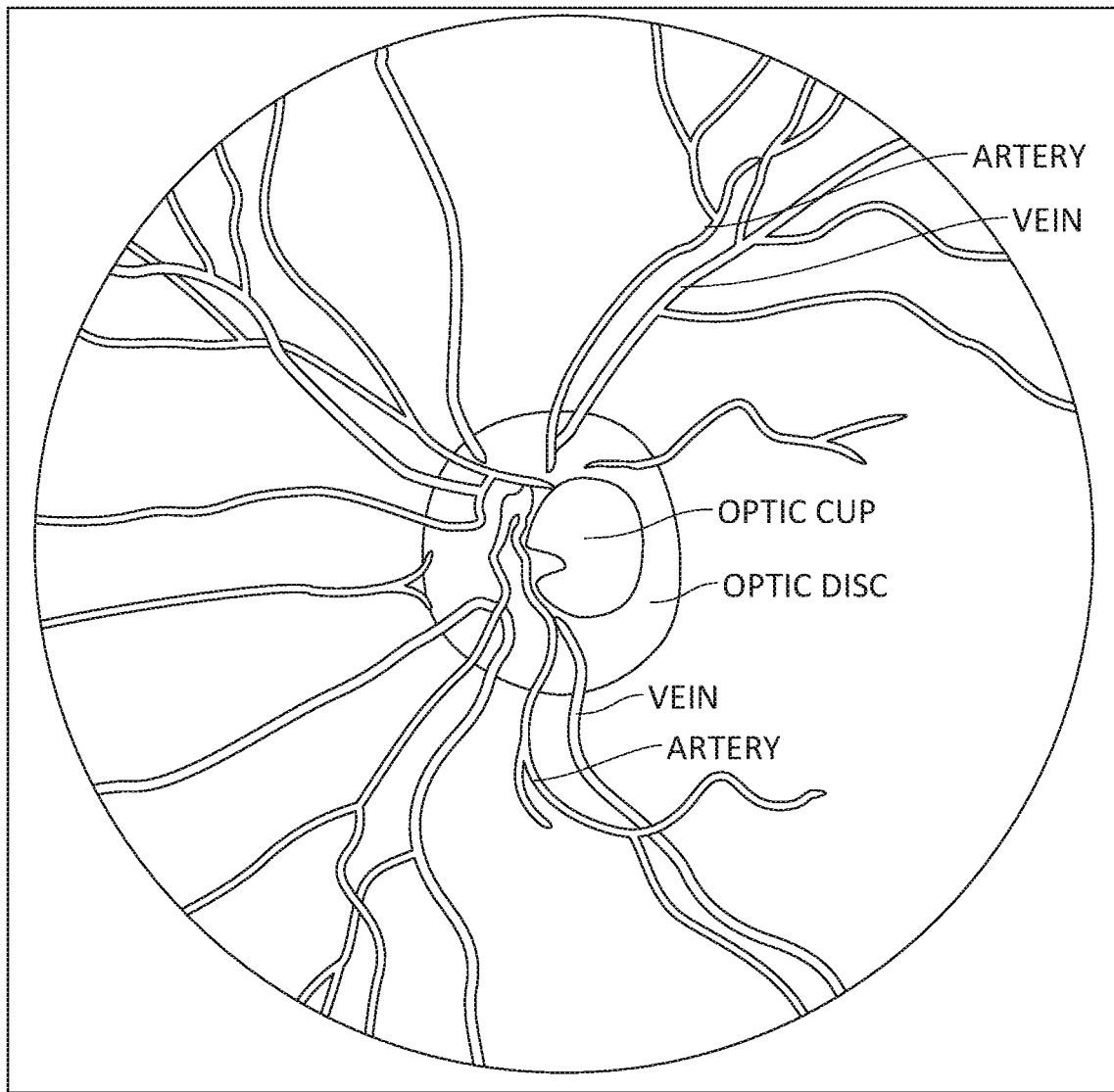
FIG. 1 is an illustration of a healthy fundus.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Medical imaging is frequently used to diagnose a disease. Mistakes interpreting medical imagery can lead to misdiagnoses of patients, which can 1) harm patients, 2) create extra cost for hospitals, and 3) undermine public trust. This is true regardless of the process by which diagnostic decisions are made: a mistake made by a human doctor has the same potential negative effects as a mistake made by a machine learned model that is using medical imagery to make diagnostic predictions. In this application, therefore, techniques are disclosed for validating machine learned models, both before and after they are deployed, so as to reduce the number of mis-diagnostic predictions.

It is difficult to monitor the performance of a machine learning model after deployment, especially when faced with a wide variety of environments in which the model is deployed. Among other factors, different patient demography and different skill levels of technicians operating the equipment can all contribute to the degradation of performance. For example, a machine learning model trained on input data consisting of patients of a particular race (e.g., Asian), can show a degradation of performance when receiving input data consisting of patients of a different race (e.g., Caucasian). In another example, a new technician may generate images having a field of view missing from the input data the machine learning model has encountered so far. This change also can result in degradation of the performance of the machine learning model.

Accordingly, techniques presented here include post-deployment validation processes that accomplish two goals: first, to assess quality of input provided to the machine learning model, and second, to detect a deviation from the expected performance as defined by pre-deployment validation. If the former issue—a drop in input quality—is detected by post-deployment monitoring, the relevant parties can be notified to make changes (e.g., the technician taking images can be re-trained). If the latter issue—a deviation from the expected performance—is detected by post-deployment monitoring, then actions can be taken to identify where the machine learning model needs to be improved (e.g., the model needs to be trained on more images of Caucasian patients).

In post-deployment validation, the validation process monitoring can include, for example: (1) monitoring to ensure a model performs as well as a reference member such as another machine learning model or a healthcare professional, and (2) monitoring to detect anomalies in data. After a model has been deployed for some time, there will be a trend in the diagnoses made, and the validation process described in this application can detect anomalies in the trend.

In some embodiments, the introduced techniques can further enable health care professionals to identify one or more possible root causes for the degradation of machine learning model's performance, and possible solutions to the problems. As discussed above, two possible reasons for an anomaly in incoming data can be: a) a hospital begins targeting a new population that has a very high prevalence of a disease, or b) a new technician is taking retinal images that have poor quality. In an automated fashion, the introduced techniques can help distinguish and identify which one of these reasons is adversely affecting the quality of the diagnosis. Further, the introduced techniques may suggest a corresponding solution based on the knowledge of the root cause (e.g., gained from separate machine learning training). For example, in case a), the knowledge of an anomaly might help provoke hospital to hire more doctors to address that disease, and in case b), the knowledge would allow the hospital to retrain the technician taking photos.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling, either direct or indirect, between two or more elements. The coupling/connection can be physical, logical, or a combination thereof. For example, two devices may be communicatively coupled to one another despite not sharing a physical connection.

When used in reference to a list of multiple items, the word "or" is intended to cover all of the following interpretations: any of the items in the list, all of the items in the list, and any combination of items in the list.

Overview

In the following description, the example of fundus imagery is used, for illustrative purposes only, to explain various aspects of the techniques. Note, however, that the techniques introduced here are not limited in applicability to fundus imagery.

FIG. 1 is an illustration of a healthy fundus. Color Fundus Retinal Photography uses a fundus camera to record color images of the condition of the interior surface of the eye, to detect the presence of illnesses. A fundus camera or retinal camera is a specialized low power microscope with an attached camera designed to photograph the interior surface of the eye, including the posterior pole (i.e., the fundus). The resulting image can be used to detect conditions such as diabetic retinopathy, age related macular degeneration, macular edema, retinal detachment, etc.

The diagram in FIG. 1 shows a healthy eye, and various features of a healthy eye visible in fundus photographs, such as the optic cup, the optical disk, arteries, veins, etc. The features labeled in the diagram can be used by a machine learning model in order to diagnose various diseases.

Figures 2A, 2B:
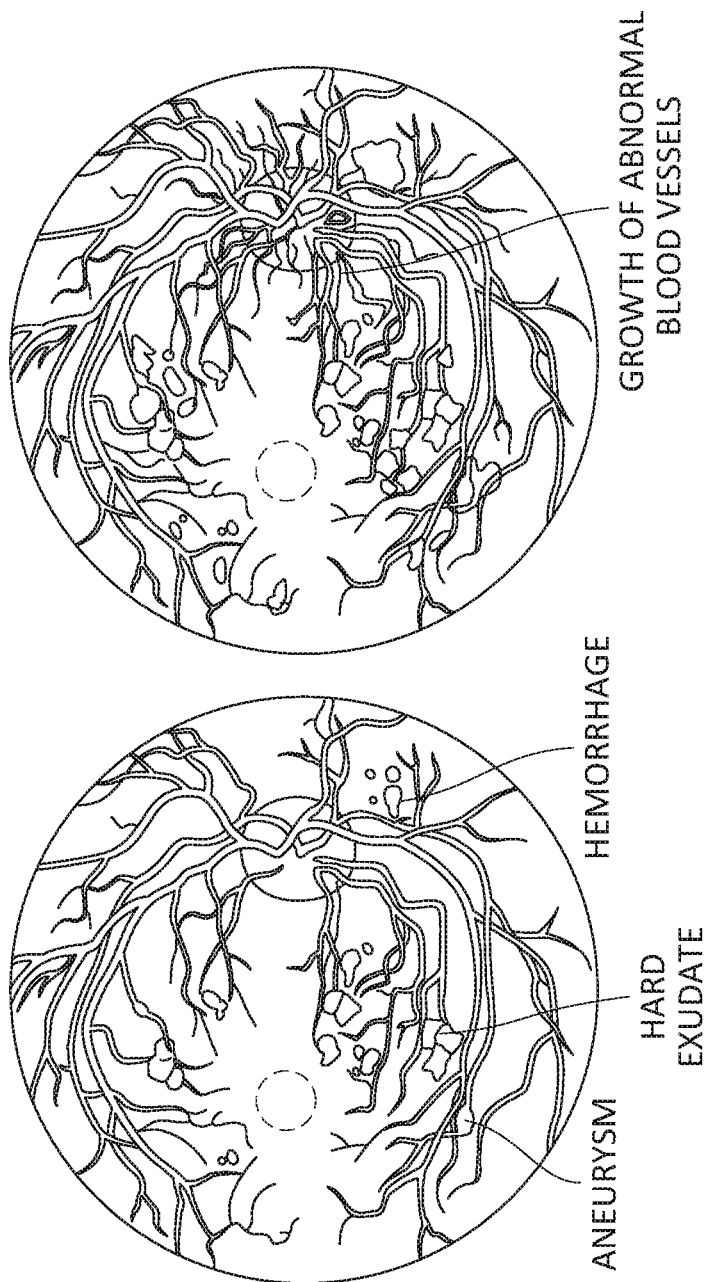
FIGS. 2A-2B illustrate example features indicative of non-proliferative and proliferative diabetic retinopathy in a fundus photograph.

FIGS. 2A-2B illustrate features indicative of non-proliferative and proliferative diabetic retinopathy that trained medical professionals look for in fundus photographs to determine how severe the disease is in a patient. A machine learned model can be trained using fundus photographs to determine how severe a disease is in a patient. Notably, the machine learned model may or may not be using the same features that a doctor uses; the machine learning model might identify that certain pixels are relevant to its decision, but does not necessarily have a concept that those pixels are related to a feature such as a hard exudate.

When the eye is diseased, the fundus photograph shows features indicative of the disease such as an aneurysm, a growth of abnormal blood vessels, a hemorrhage, a hard exudate, etc. Hard exudates are small white or yellowish white deposits with sharp margins. Often, they appear waxy, shiny, or glistening. They are located in the outer layers of the retina, next to the retinal vessels. A machine learning model can be trained to identify pixels on the fundus photograph that might capture these features.

Figure 3:
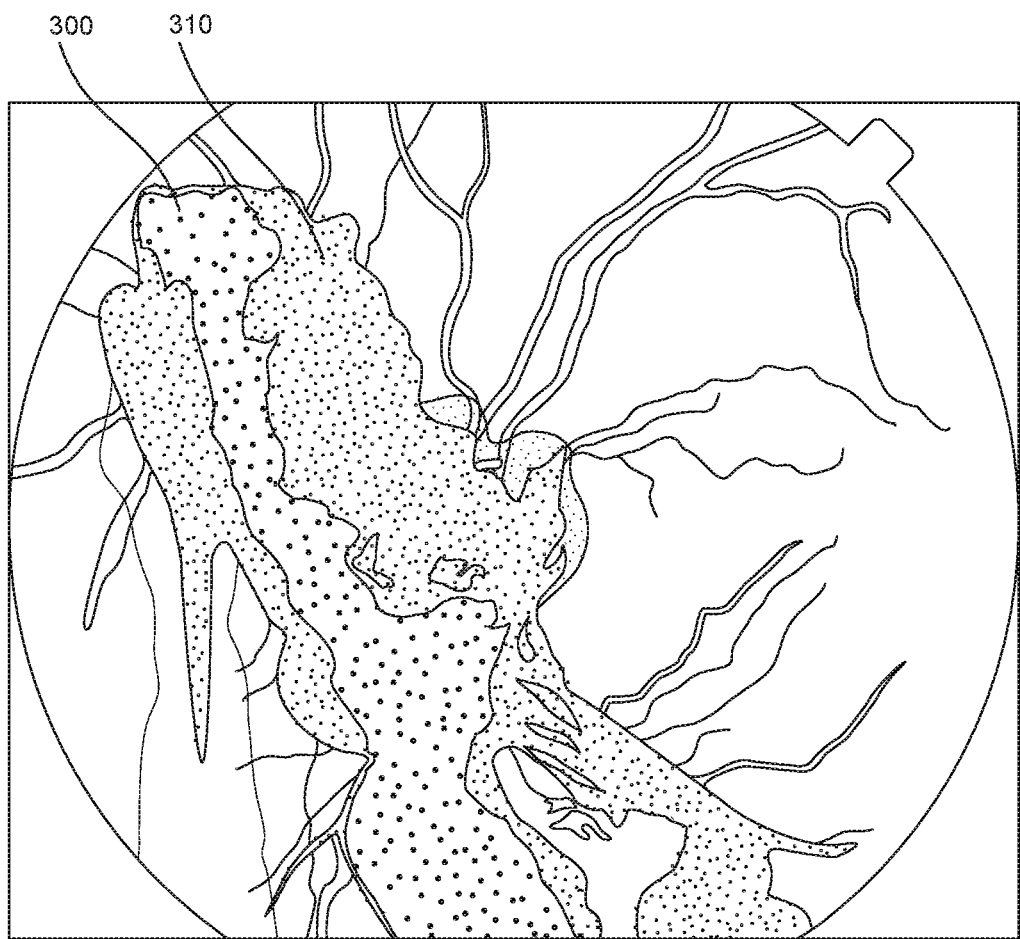
FIG. 3 depicts an example of a fundus indicative of cytomegalovirus retinitis.
Figure 4:
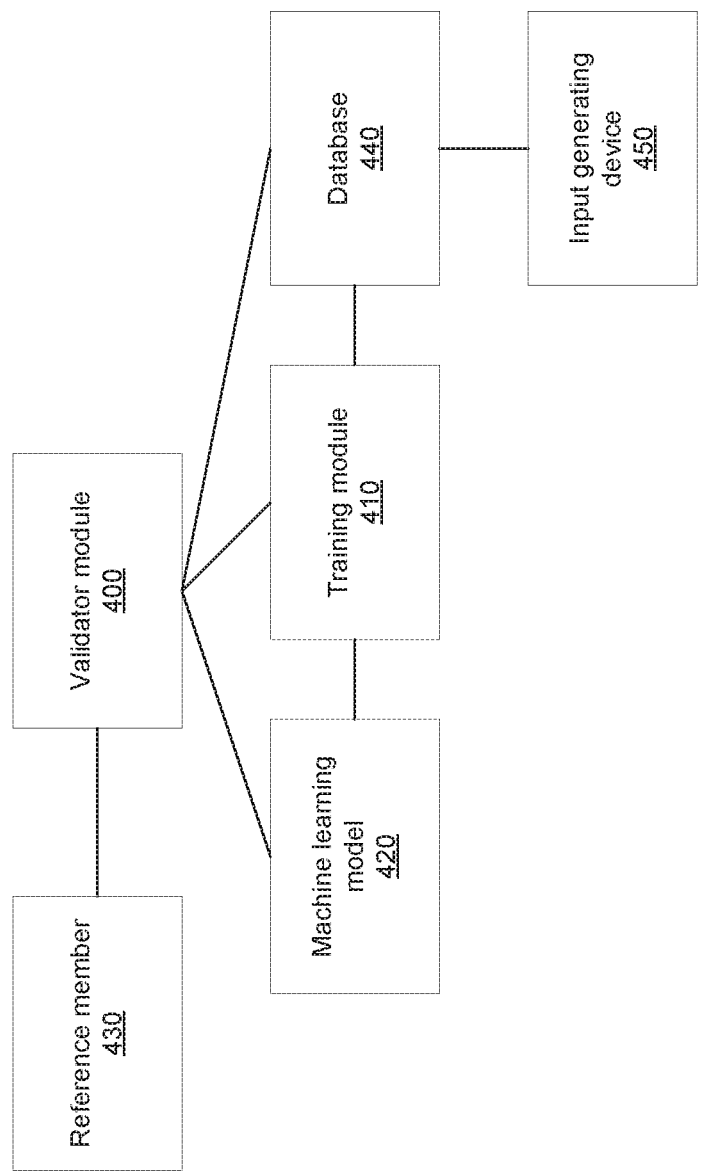
FIG. 4 shows an example system to validate a machine learning model prior to deployment.

FIG. 3 depicts an example of a fundus photograph indicative of cytomegalovirus retinitis. Cytomegalovirus retinitis is an inflammation of the retina of the eye that can lead to blindness. The features 300 and 310 are regions of discoloration of the eye in the fundus photograph. The features 300, 310 are indicative of the cytomegalovirus retinitis, and can be used by a trained machine learning model predict whether a patient has this disease and how severe the disease is Pre-Deployment Validation FIG. 4 shows a system to validate a machine learning model prior to deployment. The system includes a validator module 400, a training module 410, a machine learning model 420, a reference member 430, a database 440, and an input generating device 450.

The input generating device 450 can be a camera, a microscope, an audio recorder, an X-ray machine, a magnetic resonance imaging (MRI) machine, an ultrasound machine, etc. The input generating device 450 can generate the input such as an image, an audio file, a text, etc., which can be stored in the database 440 for later retrieval.

The reference member 430 can be another machine learning model, the machine learning model 420 at a prior time, or an interface to a professional trained to classify inputs. For example, when the reference member 430 is another machine learning model, the other machine learning model can be a more complex machine learning model having a higher accuracy, but perhaps with another drawback, such as higher latency. The output of the more complex machine learning model can be used to train the machine learning model 420. Also, the reference member 430 could be a legacy machine learning model, operable only on specific hardware, while the machine learning model 420 is operable on a more modern hardware. Similarly, when the reference member 430 is the machine learning model 420 at a prior time, the machine learning model at the prior time could have higher accuracy, but also higher latency, and the machine learning model 420 is an attempt to improve the latency of the older version.

The training module 410 can train the machine learning model 420 to diagnose various diseases such as cancer, diabetic retinopathy, hemorrhage, etc., from a variety of medical imagery. The validator module 400 can evaluate (1) a process used to create the machine learning model 420 and (2) a performance of the machine learning model 420. The model performance in pre-deployment can be evaluated based on the accuracy of inferences and/or based on the latency of inferences performed by the machine learning model.

To evaluate the process by which the machine learning model 420 is created, the validator module 400 can confirm that an appropriate optimization technique was used when creating the machine learning model 420. For purposes of discussion herein, the term "appropriate optimization technique" is referred to as any suitable technique, or any combination of technique sets, that can be used to improve and/or optimize a resulting machine learning model specifically for the deployment to a particular field of medical diagnostics (e.g., medical imaging diagnostics). It is recognized in the present disclosure that, during the training and generation phase of machine learning models, the use of a combination of the various optimization techniques disclosed here can result in particularly desirable (e.g., high accuracy and/or low latency) machine learning models. According to the present disclosure, example appropriate optimization techniques (or a combination thereof) that can generate particularly desirable results, at least for medical imaging diagnostics, can include: identifying an optimal checkpoint from which the machine learning model is preferably created, tuning hyperparameters used in training (e.g., in relation to FIG. 5 below), and/or evaluating a gain in performance (e.g., an increase in accuracy and/or a reduction in latency) produced by the machine learning model transformation methodologies. Example machine learning model transformation methodologies include ensembling or co-distilling, as described below in this application (e.g., in relation to FIGS. 8-9 below). It is noted here that various techniques may be described herein separately (e.g., in terms of functional modules); however, the introduced modules can work in a collective manner toward the same goal of increasing accuracy and reducing latency of the resulting machine learning model, so that in the end, the finally selected model (e.g., for deployment) may have the highest accuracy and/or the lowest latency.

Checkpoints are versions of models created during training. Models created at different checkpoints have varying accuracy. An initial checkpoint is used as a starting point during the training process. The initial checkpoint can be a version of a previously trained machine learning model used for a similar task. For example, if the machine learning model 420 receives images as input, the initial checkpoint can be a machine learning model trained to receive images as input and identify features such as edges and orientations within the image. In another example, if the machine learning model 420 receives audio as input, the initial checkpoint can be a machine learning model trained to receive audio files as input and identify speakers within the audio file. In another embodiment, the initial checkpoint can be a machine learning model trained to perform the same task.

An optimal checkpoint is one that is picked because it predicts features for datasets with high accuracy. Accuracy can be computed any number of ways: for example, it can be computed across one or across a variety of features; and the checkpoint success criteria could be defined as the highest average performance over all features, or, all features above various thresholds.

When optimal checkpoint selection is performed as an automatic part of training, it 1) provides a robust, reproducible way to select checkpoints, and 2) when used as a stopping condition for training, it can reduce the number of steps that a model is trained for, which reduces overall training time.

The optimal checkpoint is a version of the candidate machine learning model having passed one or more rules confirming that such version has not been overfitted to a training data set. For purposes of the discussion here, the term "overfitted" (or its variants, e.g., overfitting) refers to the situation where an candidate machine learning model produces a very small error on the training set, but when new data is presented to the candidate machine learning model the error is large. The overfitted candidate machine learning model has memorized the training examples, but it has not learned to generalize to new situations. Note that the optimal checkpoint may or may not be the last iteration of the training process because the system can produce several more iterations (i.e., checkpoints) of the candidate machine learning model before determining that the last few iterations started to overfit. The optimal checkpoint can be selected by analyzing changes in an accuracy-related metric of versions of the candidate machine learning model corresponding to successive iterations of the training process.

To evaluate the performance, the validator module 400 can compare an accuracy and a latency of the machine learning model 420 in generating the inference to that of a second machine learning model, such as the reference member 430. The validator module can ensure that the method by which the performance of a model is calculated is both sanitary and comprehensive. To ensure the calculation is sanitary, no medical imagery present in the dataset on which a model was trained can be present within the validation dataset, moreover no medical imagery from a single patient can be present in both training and validation datasets (e.g., left retinal image in the training dataset, and right retinal image in the validation dataset); this may pollute the calculation of the performance of the model. With regard to ensuring the method is comprehensive, the validator module can ensure that the dataset used to calculate the performance of the model covers all predefined categories of patients. For instance, the validation dataset can contain instances of all genders, races, ethnicities, etc. that will be present in the actual patient population that will be diagnosed by the machine learned model.

In one or more examples, the validator module 400 can select a dimension to use in comparing the machine learning model 420 with the reference member 430. In statistics, machine learning and information theory, the "dimension" of the data refers to the number of random variables that are under consideration or analysis in the data. The term "dimension" is sometimes also referred to in the art as "feature" or "attribute." For example, the dimension can be a gender of a subject used to generate the input, an age of the subject, a race of the subject, an ethnicity of the subject, or a type of a device used to obtain the input. According to one or more embodiments, the dimension that can be selected by the validator module 400 can include an attribute of the input, an attribute of the input generating device 450, an attribute of a subject from which the input was generated, etc. Additionally or alternatively, the attribute of the input can be a modality of the input, a field of view of the input, an eye position, etc. The attribute of the device generating the input can be a type or a model of the camera generating the input, and the camera's related specification. The attribute of the subject from which the input was generated can be a race, a gender, and ethnicity, current health condition, health history, age, location of residence, etc. For example, the validator module 400 can select inputs associated with a particular dimension, such as only subjects over 60 years of age, or only subjects suffering with HIV/AIDS. The dimension for validation should be selected with the target patient population in mind. Additionally, the sample size (i.e., number of inputs) needs to be sufficiently large so that any dimension value drop is significant enough to justify further investigation.

Once the one or more dimensions are selected, using only the inputs associated with the dimension, the validator module 400 can tune the performance of the machine learning model 420, or the validator module 400 can compare the performance of the machine learning model 420 to a performance of the reference member 430. By using only the inputs associated with the dimension, fine-tuning of the machine learning model 420 performance in the particular dimension can be performed efficiently. To tune the performance or compare the performance of the machine learning model 420, the validator module 400 can use specificity and sensitivity of the machine learning model 420, as described in this application (e.g., in relation to FIGS. 6-7 below).

Figure 5:
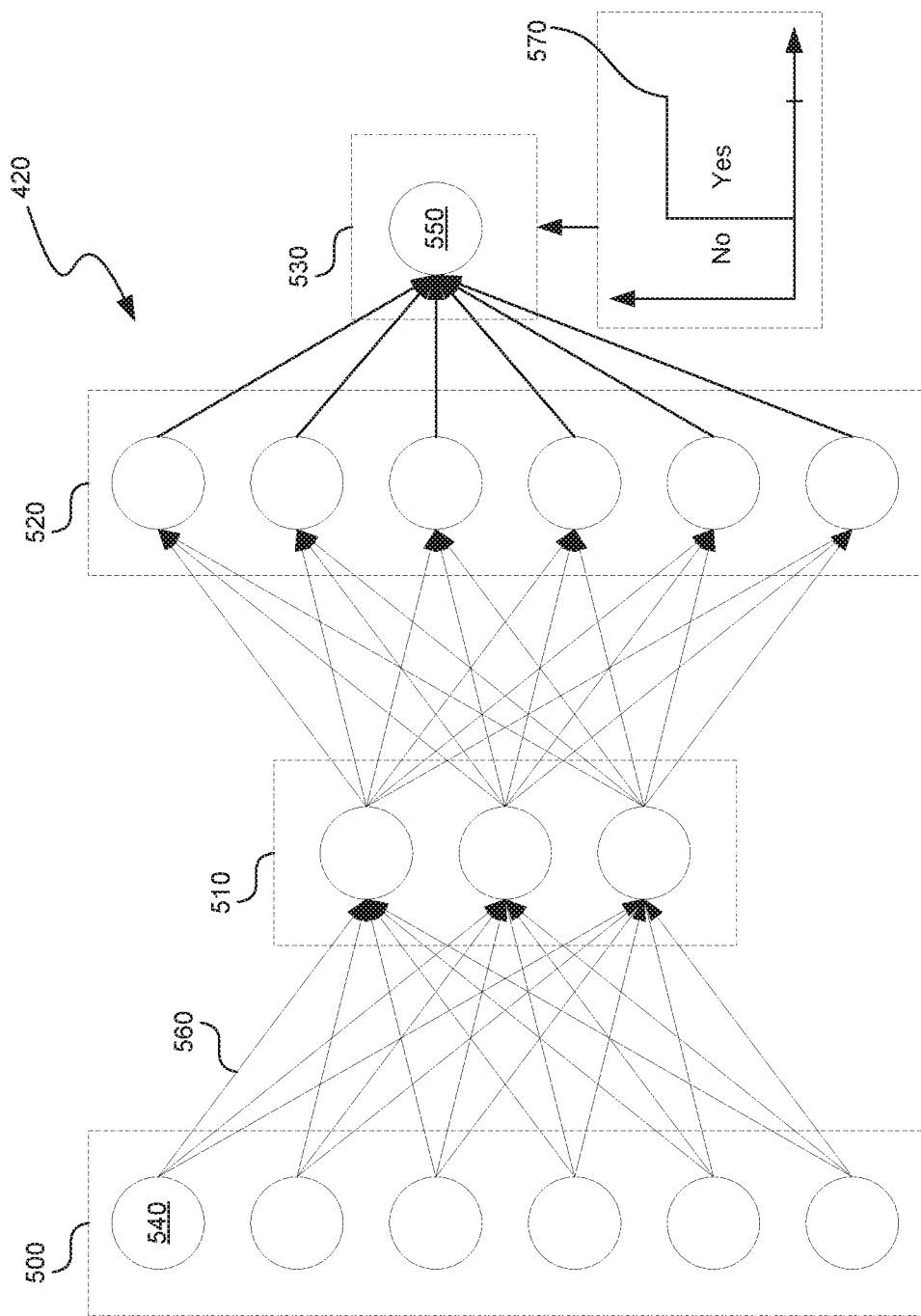
FIG. 5 shows an example machine learning model.

FIG. 5 shows an example of the machine learning model 420 in FIG. 4. The machine learning model shown in FIG. 5 is neural network based; however, other suitable machine learning models may be applicable in a similar manner. The machine learning model 420 can contain multiple layers 500, 510, 520, 530 of neurons 540, 550 (only two labeled for brevity). The neurons 540, 550 in each layer can be connected to all the neurons in the subsequent layer with connections 560 (only one labeled for brevity). Connections 560 can be weighted with predetermined values, e.g., between −1 and 1, or 0 and 1. The output layer 530 can contain one or more neurons 550. The output neuron 550 can produce an output value, e.g., between 0 and 1. A threshold 570 can be applied to the value of the output neuron to produce an inference.

For example, the inference can indicate whether the input contains a specific feature or not. In a more specific example, a model score classification threshold ("threshold") of 0.6 specifies that if the output value is less than or equal to 0.6, the feature is not identified, while if the output value is greater than 0.6, the feature is identified. The feature can be a presence of a disease in the medical image. During training, the training module 410 in FIG. 4 can select an appropriate value for the threshold 570. To select the threshold 570, the training module 410 can artificially weigh the inference of the machine learning model towards a false positive or a false negative based on a user preference. For example, if a hospital advises that false positives are preferable to false negatives, the training module 410 can decrease the threshold. As shown in FIG. 5, the threshold 570 is weighted towards false positives, because the area denoting "yes" under the threshold 570 is greater than the area denoting "no" under the threshold 570. That is to say, the threshold defines whether an inference from an output of a model is to be positive or negative. In one or more implementations, below the threshold, an inference by a candidate machine learning model is defined as a negative, and above the threshold, the inference by the candidate machine learning model is defined as a positive.

In addition, during training, the training module 410 can also select the appropriate hyperparameters for the machine learning model 420. In machine learning and for purposes of discussion here, a hyperparameter is a parameter whose value is set before the learning process begins. By contrast, the values of other parameters (e.g., weights in a model) are derived via training. The hyperparameters can indicate the number of layers 500, 510, 520, 530 contained in the machine learning model 420, and a number of neurons 540, 550 contained in each layer 500, 510, 520, 530. In other words, the number of layers can represent one hyperparameter, and the number of neurons per layer can represent another hyperparameter independent of the first hyperparameter.

To select the hyperparameters, the training module 410 can create multiple models with various hyperparameters. Each model can have varying number of layers 500, 510, 520, 530 and varying number of neurons 540, 550 contained in each layer 500, 510, 520, 530. Consequently, the multiple models can vary in accuracy and/or latency. The training module 410 can train the multiple models on the same inputs, and measure the performance of the multiple models at the end of the training. The various machine learning models with varying hyperparameters can have different accuracy and latency. Accuracy can be measured as a number of responses matching the responses of the reference member. Latency can be measured as an amount of time to generate an inference. In the end, the training module 410 can select only the substantially optimal machine learning models, namely those with the highest accuracy and lowest latency. For example, the substantially optimal machine learning models can be selected as the machine learning models having accuracy above a minimum threshold such as 60% and having a latency below a maximum threshold such as 5 hours.

Figure 6:
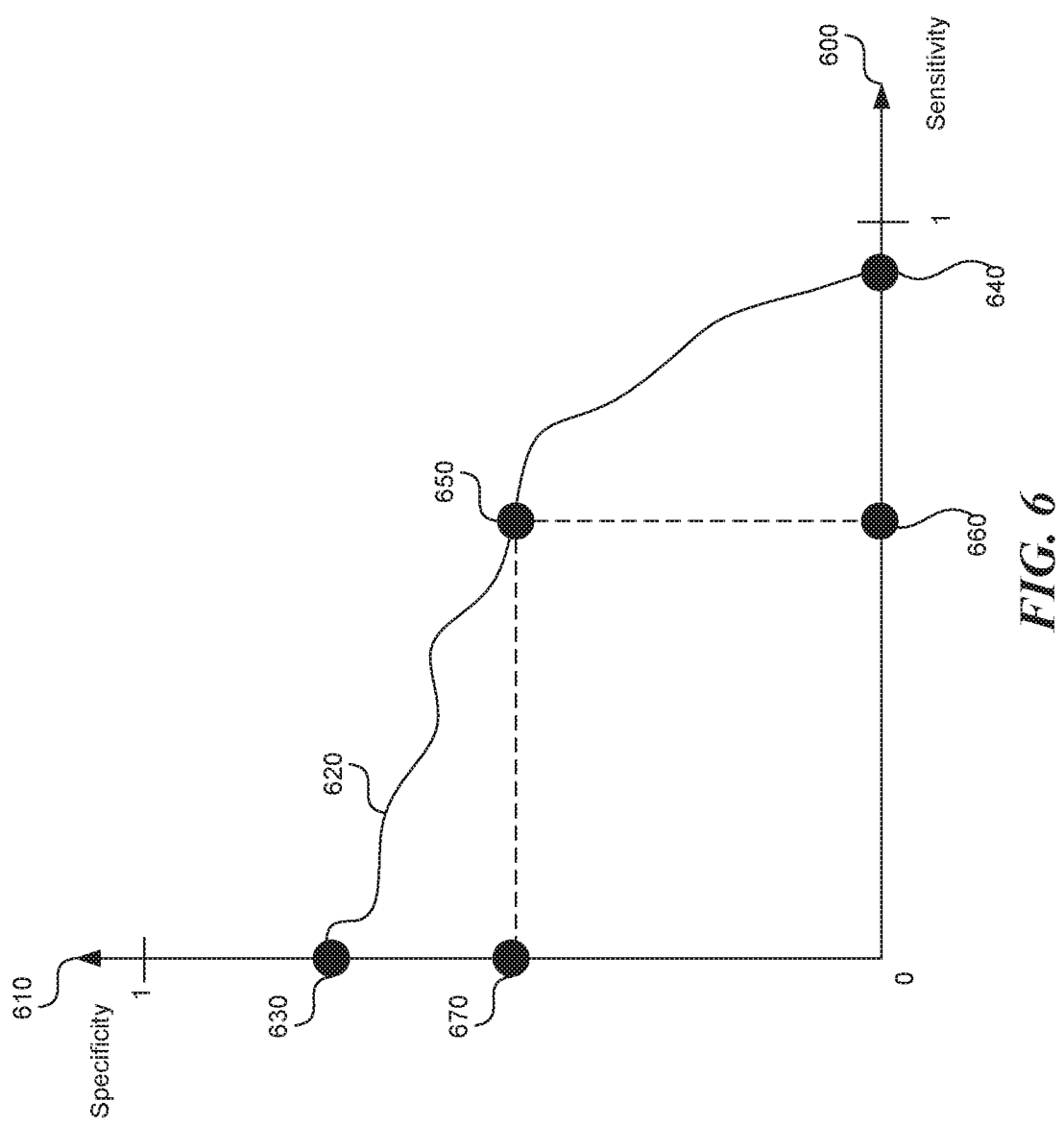
FIG. 6 shows an example of using the specificity and sensitivity of a machine learning model to improve the machine learning model's performance.

FIG. 6 shows using the specificity and sensitivity of a machine learning model to improve the machine learning model's performance. Sensitivity 600 of the machine learning model measures the proportion of positives that are correctly identified as such (e.g., the percentage of sick people who are correctly identified as having the condition). Specificity 610 measures the proportion of negatives that are correctly identified as such (e.g., the percentage of healthy people who are correctly identified as not having the condition). Alternatively, specificity 610 can be defined as (1−the false positive rate). Sensitivity 600 and specificity 610 can be measured between 0 and 1. Sensitivity 600 and specificity 610 tend to be inversely correlated, and as one increases, the other decreases.

Sensitivity 600 and specificity 610 vary as the threshold 570 in FIG. 5 varies from the lowest possible value to the highest possible, thus generating the graph 620. For example, assume that the output range of the neuron 550 in FIG. 5 is between 0 and 1. When the threshold 570 is set to 0, value 630 is obtained, while when the threshold 570 set to 1, value 640 is obtained.

To initialize the training process, the machine learning model 420 can select the desired value of either sensitivity 600 or specificity 610, determine the appropriate threshold and adjust the threshold based on further training and validation. The training module 410 in FIG. 4 can measure a sensitivity 600 and specificity 610 for each of the machine learning model 420 and the reference member 430 in FIG. 4 as the threshold 570 varies. The training module 410 can compare the inference of the machine learning model 420 to an inference of the reference member 430 when both the machine learning model 420 and the reference member 430 receive substantially identical input. The training module 410 can select the threshold 570 producing a highest number of matching inferences between the inferences of the machine learning model 420 and the inferences of the reference member 430. The selected threshold 570 determines a point 650 on of the graph 620. The point 650 determines the sensitivity 660 and specificity 670 of the machine learning model 420.

Figure 7A:
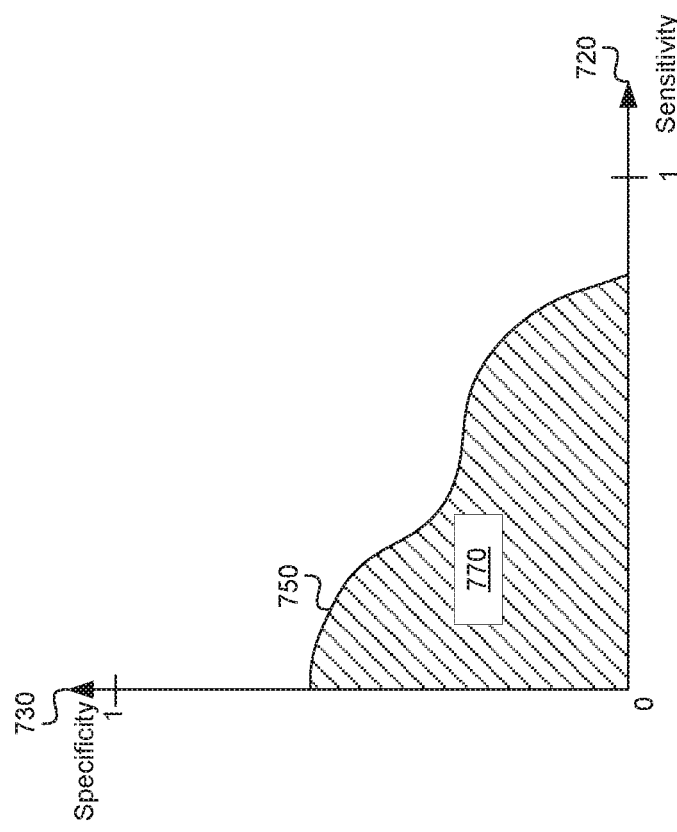
FIGS. 7A-7B show sensitivity and specificity used in comparing a performance of two machine learning models.
Figure 7B:
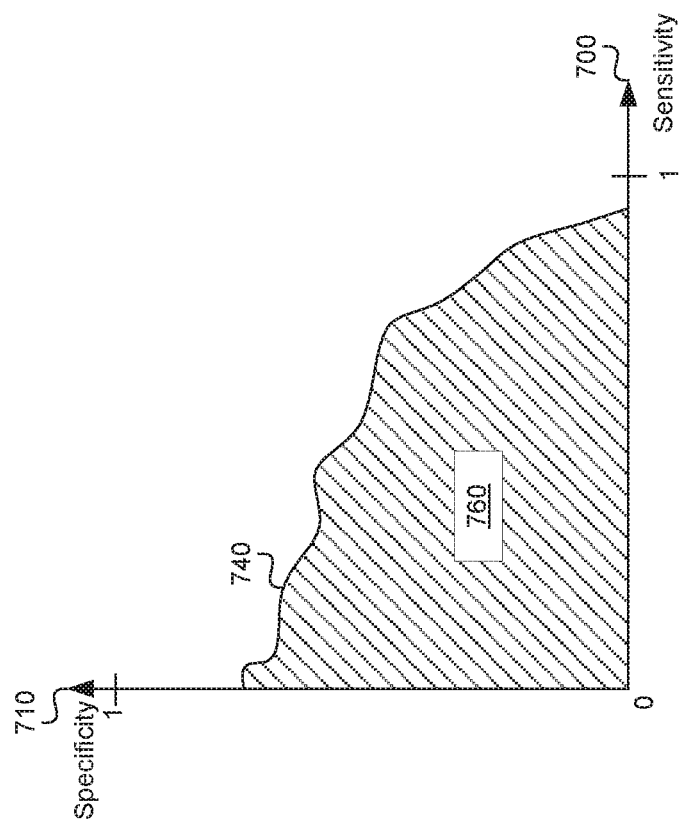

FIGS. 7A-7B show sensitivity and specificity used in comparing a performance of two machine learning models. FIG. 7A shows sensitivity 700 and specificity 710 associated with the machine learning model 420 in FIG. 4. FIG. 7B shows sensitivity 720 and specificity 730 associated with the reference member 430 in FIG. 4. The validator module 400 can select inputs into the associated with a particular dimension, such as only fundus images of subjects over 60 years of age, or only fundus image of subjects suffering with HIV/AIDS. Based on the selected dimension, the validator module 400 can measure a sensitivity 700 and a specificity 710 of the machine learning model 420 as a threshold 570 in FIG. 5 of the machine learning model 420 varies. Further, based on the selected dimension, the validator module 400 can measure the sensitivity 720 and specificity 730 of the reference member 430 as a threshold 570 associated with the output of the reference member 430 varies. As a result, the validator module 400 can generate a graph 740 representing a relationship between sensitivity 700 and specificity 710 of the machine learning model 420 for a particular dimension. The particular dimension can be age, health status, race, ethnicity, gender of the subject, a type of device used to record the input such as the type of camera used to create the fundus photograph, etc. Similarly, the validator module 400 can generate a graph 750 representing a relationship between sensitivity 720 and specificity 730 of the reference member 430 for a particular dimension. The graphs 740, 750 can be receiver operating characteristic (ROC) curves. In statistics, a receiver operating characteristic curve, i.e. ROC curve, is a graphical plot that illustrates the diagnostic ability of a binary classifier system as its discrimination threshold is varied.) The particular dimension can be age, health status, race, ethnicity, gender of the subject, a type of device used to record the input such as the type of camera used to create the fundus photograph, etc.

Based on the measured sensitivity 700 and specificity 710 of the machine learning model 420, the validator module 400 can generate a machine learning model accuracy metric representing a correctness of inferences produced by the machine learning model 420. In a similar manner, based on the measured sensitivity 720 and specificity 730 of the reference member 430, the validator module 400 can generate a reference member accuracy metric representing a correctness of inferences produced by the reference member 430. The accuracy metrics 760, 770 can be calculated as the areas under the graphs 740, 750. The greater the area under the graph 740, 750, the greater the accuracy metrics 760, 770. For example, the area 760 under the graph 740 in FIG. 7A is greater than the area 770 under the graph 750 in FIG. 7B, thus indicating that the machine learning model 420 is more accurate than the reference member 430.

In addition to the accuracy metrics 760, 770, the latency of the machine learning model 420 and the reference member 430 can be taken into account in determining which model has a better overall performance. The validator module 400 can select for high accuracy and low latency.

If the validator module 400 determines that the machine learning model 420 is underperforming in a particular dimension, such as a particular field of view of the camera capturing the fundus image, the validator module 400 can alert the training module 410 to further train the machine learning model 420 by providing more training data to the machine learning model 420 containing the problematic field of view.

Figure 8:
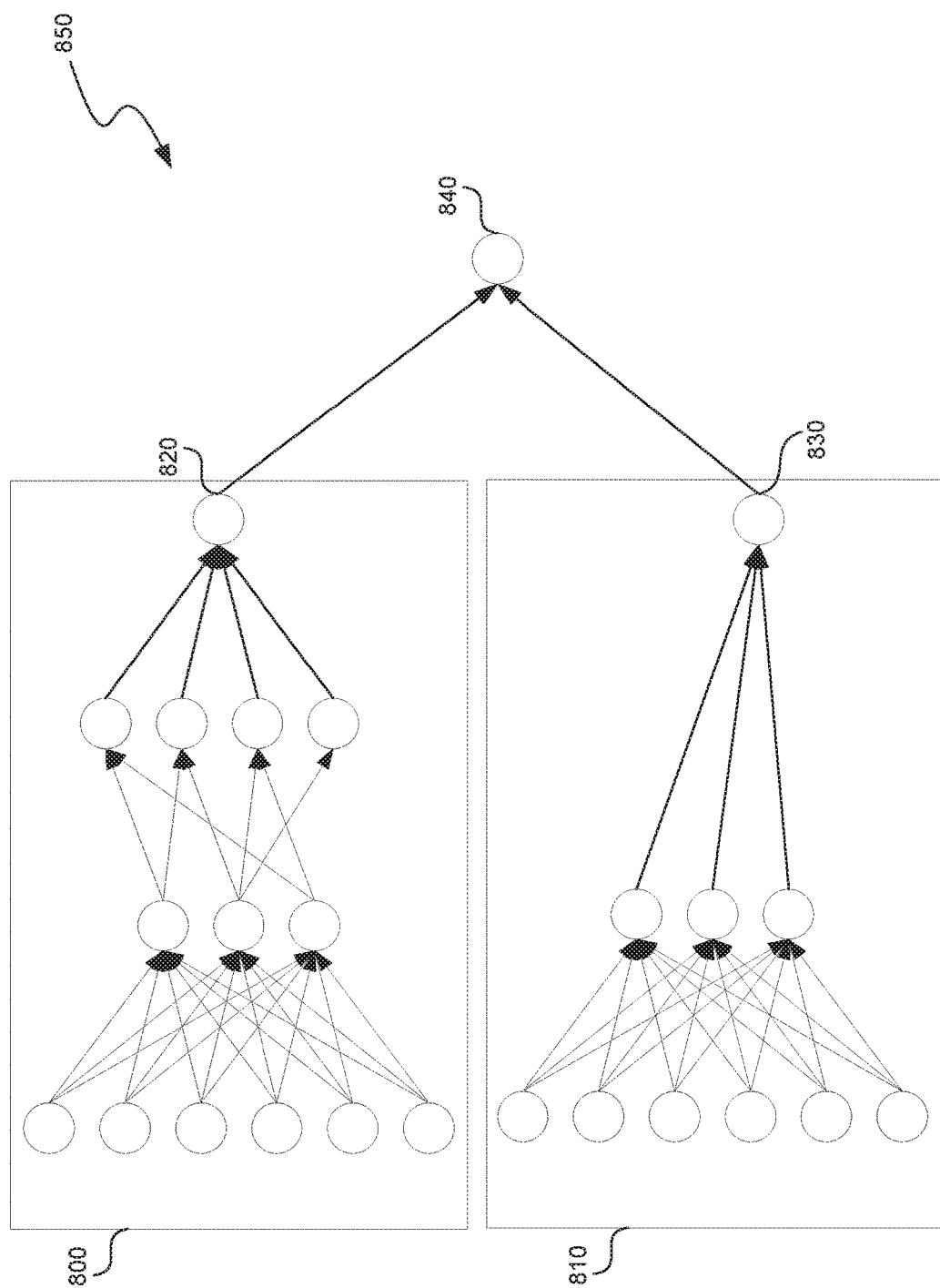
FIG. 8 shows an example of an ensembled machine learning model.

FIG. 8 shows an example of an ensembled machine learning model. In statistics and machine learning, ensemble methods use multiple learning algorithms to obtain better predictive performance than could be obtained from any of the constituent learning algorithms alone. The training module 410 in FIG. 4 can ensemble multiple component machine learning models 800, 810 to obtain the ensembled machine learning model 850 by combining multiple outputs 820, 830 associated with the multiple component machine learning models 800, 810. In some embodiments, the multiple machine learning models 800, 810 can include ten machine learning models.

In some examples, the machine learning model 850 can be the machine learning model 420 in FIG. 4. Every individual component model 800, 810 in the multiple machine learning models can take a slightly different training path, and thereby be better at predicting a particular dimension. For example, machine learning model 800 can receive more inputs associated with the particular type of input device, while the component machine learning model 810 can receive more inputs associated with a particular type of disease. As a result, the accuracy of the ensembled machine learning model 850 is greatly improved compared to the accuracy of each individual component model 800, 810.

By combining multiple (e.g., ten) component individual models 800, 810, machine learning model 850 effectively improves the performance in various dimensions. To obtain the final output 840, the outputs 820, 830 of the multiple individual models 800, 810 are averaged. For example, when an input, such as an image, is provided to each of the individual component models 800, 810, each individual component model 800, 810 within the ensemble provides the output 820, 830. The outputs from the individual component models 800, 810 can be interpreted as votes, each vote stating, "this image has a X % chance of having proliferative diabetic retinopathy." The final output 840 of the ensemble can be an average of all these votes.

The validator module 400 in FIG. 4 can identify how many individual models 800, 810 to ensemble. Generally, the higher the number of individual component models 800, 810, the better the ensemble model 850 performs. However, the performance benefit can plateau after a certain number of (e.g., five or ten) individual component models 800, 810 are combined. The more individual models 800, 810 are combined, the more computational resource intensive the ensemble model 850 becomes. Roughly, an ensemble of ten individual component models 800, 810 requires five times the computing resources, such as processing power, memory, bandwidth, necessary for an ensemble of two individual component models 800, 810. The validator module 400 helps select the smallest possible ensemble that gives the highest performance. Highest performance can be a combination of high accuracy and low latency. The highest performance can be defined depending on a given field. In a field where accuracy is paramount, and latency may be less relevant, the highest performance can be defined as highest accuracy, regardless of latency. In contrast, in a field where low latency is paramount, while accuracy is desirable but less crucial, the highest performance can be defined as low latency with above average accuracy.

Figure 9:
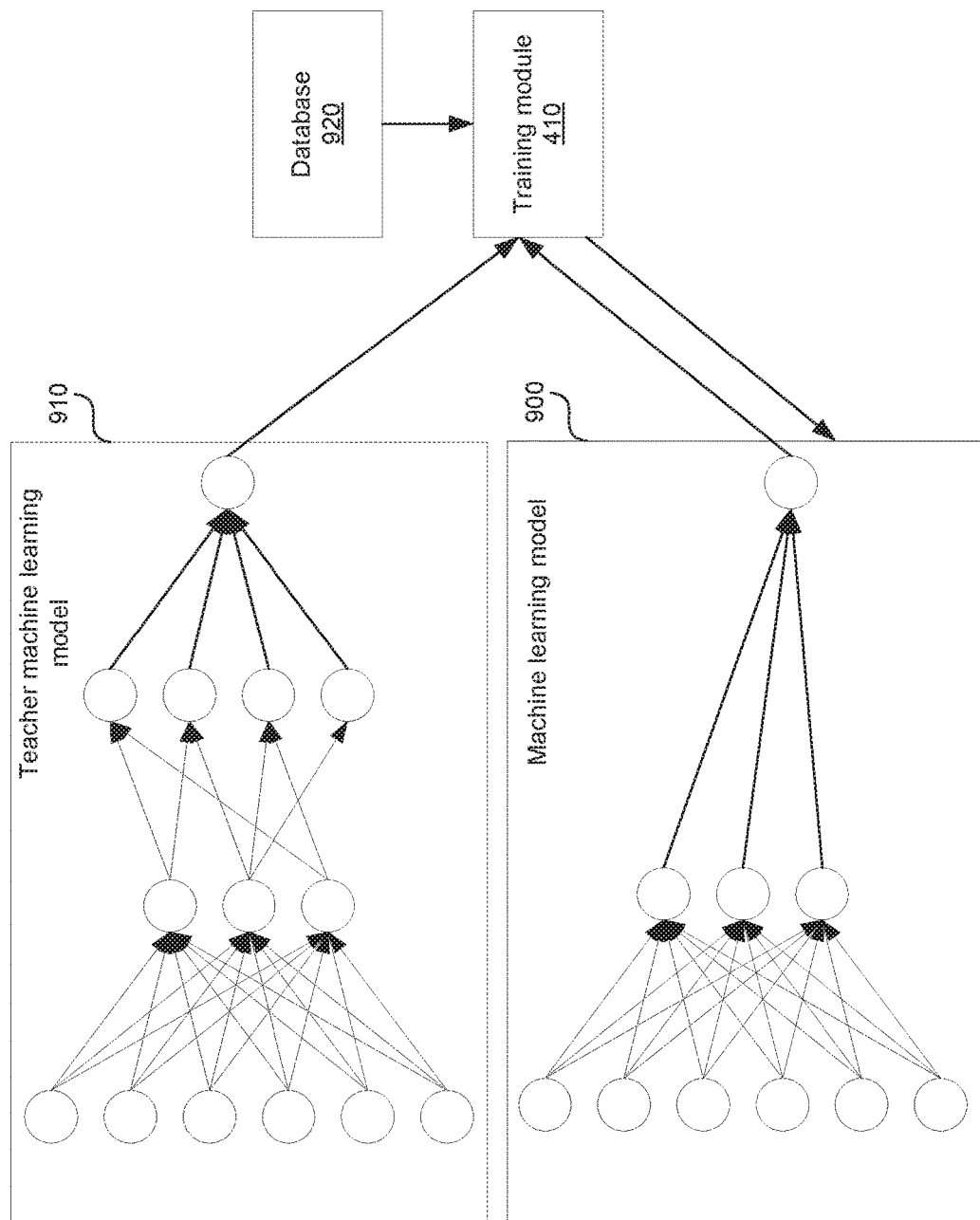
FIG. 9 shows an example process of co-distilling a machine learning model.

FIG. 9 shows a process of co-distilling a machine learning model. The training module 410 in FIG. 4 can improve the performance of the machine learning model 900 using co-distilling, namely, training the machine learning model 900 using an inference of a more computationally expensive machine learning model 910 and an inference of the reference member 430 in FIG. 4. Machine learning model 900 can be the machine learning model 420 in FIG. 4.

Co-distilling is related to ensembling. Co-distilling is a technique to improve the performance of the machine learning model 900 by training the machine learning model 900 on the inference of a more computationally expensive machine learning model 910, such as an ensembled machine learning model. Co-distilling is an attempt to achieve the same high model performance of the more computationally expensive machine learning model 910, but without requiring the intensive compute resources. The more computationally expensive model 910 can be thought of as a teacher model.

The machine learning model 900 can learn by computing a loss function, and optimizing performance to minimize the loss function. At any point in the training process, machine learning model 900 can make an inference about an input, such as an image, and compare the inference to some known ground truth, such as the inference made by the reference member 430 based on the same input. The ground truth information can be stored in a database 920, which can correspond to the database 440 in FIG. 4. The machine learning model 900 can learn from a difference between the inference it made, and the inference made by the reference member 430.

In co-distilling, the loss function can also involve an inference from the teacher model 910. For example, the teacher model 910 can make the inference about the image as well, and the training module 410 computes the loss function as the (1) difference between the machine learning model 900 and the teacher model 910, plus (2) the difference between the machine learning model 900 and the ground truth. The result is that the machine learning model 900 learns all the "complexities" that the teacher model 910 knows, without the need to be so computational expensive. Consequently, the machine learning model 900 can train faster and can execute faster. At the end of co-distilling, the validator module 400 can verify, using example techniques discussed here, that the machine learning model 900 has approximately the same performance as the teacher model 910.

Figure 10:
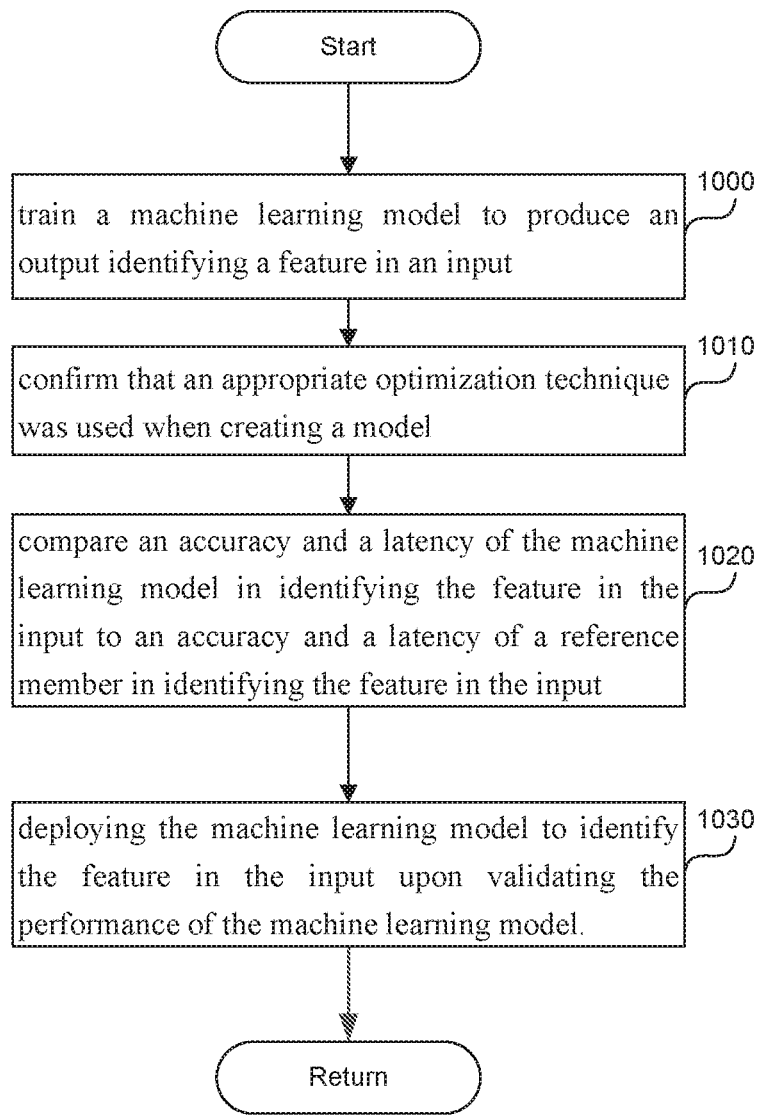
FIG. 10 is an example flowchart of a computer-implemented method validating a machine learning model prior to deployment.

FIG. 10 is a flowchart of a computer-implemented method validating a machine learning model prior to deployment. The validation process can contain two phases: (1) evaluating a process used to create the machine learning model and (2) evaluating a performance of the machine learning model, and ensuring that the method by which this performance was achieved is sanitary and comprehensive. In step 1000, a processor can train a machine learning model to produce an inference. The inference can be a diagnosis of various diseases such as cancer, diabetic retinopathy, etc.

The two phases can be performed automatically using one or more computer processors. The fact that the two faces are performed automatically enables the computer implemented method to test a large number of machine learning models, such as a 1,000,000 learning models, and select an optimal machine learning model to deploy. By contrast, selecting the best doctor out of a pool of 1,000,000 doctors is impossible because the time required to evaluate such a large pool of doctors exceeds a lifetime of a person. As a result, the inference produced by the deployed machine learning model can be superior to a doctor, and, consequently, save human lives. In step 1010, to perform phase (1) above, the processor confirms that an appropriate optimization technique is used when creating the machine learning model. The appropriate optimization technique can include: identifying the optimal checkpoint from which a model should be created, tuning hyperparameters used in training, evaluating performance gains produced by model transformation methodologies like ensembling and/or co-distilling. When one or more of the above optimization techniques have been used, the process of generating the machine learning model can become faster because less processor power, and memory is necessary in generating a deployable machine learning model.

Using either hyperparameter tuning or co-distillation (or both) can reduce the overall size of a generated model. Due to the smaller size the time of inference is reduced. These techniques can thus decrease the latency of diagnoses when a model is deployed. In a similar vein, using either ensembling or optimal-checkpoint selection (or both) can improve the accuracy of the generated model. Optimal checkpoint selection ensures a single model is achieving the highest possible accuracy. Ensembling gives insight into how the accuracy of multiple models combined improves with the number of models used in an ensemble. Optimal checkpoint selection can also reduce training time if used to distinguish a 'stopping point' for model training: rather than training for a fixed number of steps, a model can stop training as soon as its accuracy stops improving. Combining these techniques (for example, co-distilling using an ensembled model as a teacher) allows for the generation of a model that is both highly accurate and fast.

Combining all four of the above techniques (optimal-checkpoint selection, ensembling, co-distillation, and hyperparameter tuning) can result in an even more accurate and efficient candidate machine learning model because, during the step of hyperparameter tuning, multiple candidate machine learning models can be produced. By comparing an accuracy and/or latency of the multiple candidate machine learning models, the candidate machine learning model with high accuracy and low latency can be selected.

In addition, the processor can confirm that the data collected to train and evaluate the model has been labeled (and adjudicated, if required) by a professional such as a healthcare professional. Also, the processor can confirm that all necessary artifacts relevant to building the machine learning model have been recorded in a data structure that conforms with regulatory auditing, and the processes are defined to address issues with live models, including what actions are taken when initiating a recall.

Further, the processor can confirm that the dataset used to train the machine learning model comprehensively covers a diversity of expected input (e.g., images should be from the camera that is in the hospital in which the machine learning model is deployed, a specific percentage of images cover certain genders, ethnicities, races, ages, etc. so as to have coverage over all potential subjects). The processor can check that the dataset used to train the machine learning model and the data set used to validate the machine learning model do not have any overlap. In addition, the processor can check that the dataset for training and for validation is stored in an encrypted location (to protect the subject's privacy) that will exist for some number of years after a model has been deployed and deprecated (to adhere with regulatory restrictions).

In step 1020, to perform phase (2) above, the processor can compare an accuracy and a latency of the machine learning model in generating the inference to an accuracy and a latency of a reference member in generating the inference. Making the inference can include diagnosis, prognosis, companion diagnosis, disease staging, or any combination thereof. To measure the latency of the machine learning model and/or the reference member, the processor can measure the amount of time the machine learning model and/or the reference member required to produce an inference.

In one embodiment, to measure the accuracy of the machine learning model and/or the reference member, the processor can measure a specificity and a sensitivity of the machine learning model and the reference member as a threshold associated with the output of the machine learning model and the reference member varies, as described in this application. Based on the measured specificity and sensitivity of the machine learning model and the measured specificity and sensitivity of the reference member, the processor can generate a machine learning model accuracy metric and a reference member accuracy metric representing a correctness of inferences produced by the machine learning model and the reference member. The accuracy metric can be an area under the curve, as described in this application.

The processor can determine whether the machine learning model outperforms the reference member based on the machine learning model accuracy metric, the reference member accuracy metric, a latency of the machine learning model in generating the inference, and a latency of the reference member in generating the inference.

In another embodiment, to perform phase (2) above, namely to evaluate a performance of the machine learning model, the processor can compare the performance of the machine learning model to the performance of the reference member along a dimension such as a gender, a race, an ethnicity, and an age, a health condition, a type of device used to generate the input, field of view of the input, etc., to identify an area in which the machine learning model is underperforming. After identifying the underperforming area, the machine learning model can be retrained with inputs containing the problematic dimension.

In step 1030, the processor can increase an accuracy and can decrease a latency of generating the inference by deciding to deploy the machine learning model upon validating the performance of the machine learning model. The deployment can involve using the machine learning model in a hospital as a diagnostic tool.

The processor can measure a specificity and a sensitivity of the machine learning model as a threshold associated with an output of the machine learning model varies, as described in this application. The processor can compare the inference of the machine learning model to an inference of the reference member when both the machine learning model and the reference member receive substantially identical input. The processor can select the threshold which produces a substantially highest number of matching inferences between the machine learning model and the reference member. The processor can select a threshold weighing the inference towards a false positive or a false negative diagnosis based on the user preference. For example, if a hospital advises that false positives are preferable to false negatives, meaning, the hospital would prefer to diagnose healthy subjects, instead of misdiagnosing sick subjects, the threshold can be set lower to produce more diagnoses of illness.

The machine learning model can utilize certain techniques in an automated pipeline to improve the performance. The techniques include: ensembling, hyperparameter tuning, and co-distilling. Ensembling, as described in this application, can create a single super-model out of many models, which can greatly improve the performance of the super-model by promoting diversity in predictions. The processor can find the optimal number of models to ensemble into a super-model; typically, as more models are added to the super-model the performance of the super-model will increase until it reaches a saturation point. After this saturation point the model performance no longer improves. The ideal super-model is the smallest sized super-model that has reached this saturation point in performance. Hyperparameter tuning, as described in this application, can optimize parameters of the machine learning model to improve accuracy and latency. Finally, co-distilling, as described in this application, is a technique to improve the performance of a single model by training on the inference of a super-model.

The processor can record all artifacts necessary to regenerate the machine learning model. In other words, the processor can record the data that was used to train, tune and evaluate the machine learning model, as well as the binaries and versions of scripts that were run to actually perform the training, exporting and validation. The recording of the artifacts is critical for any investigations that need to be done on the machine learning model that has been deployed. Understanding what parameters, configuration, and data was used when training can shed light on why a model is over- or under-performing. If the machine learning model is not approved for deployment, the processor can identify and address areas of improvement, including tuning of hyperparameters, ensembling, co-distilling, and collecting more data from a particular dimension.

Post-Deployment Validation

Figure 11:
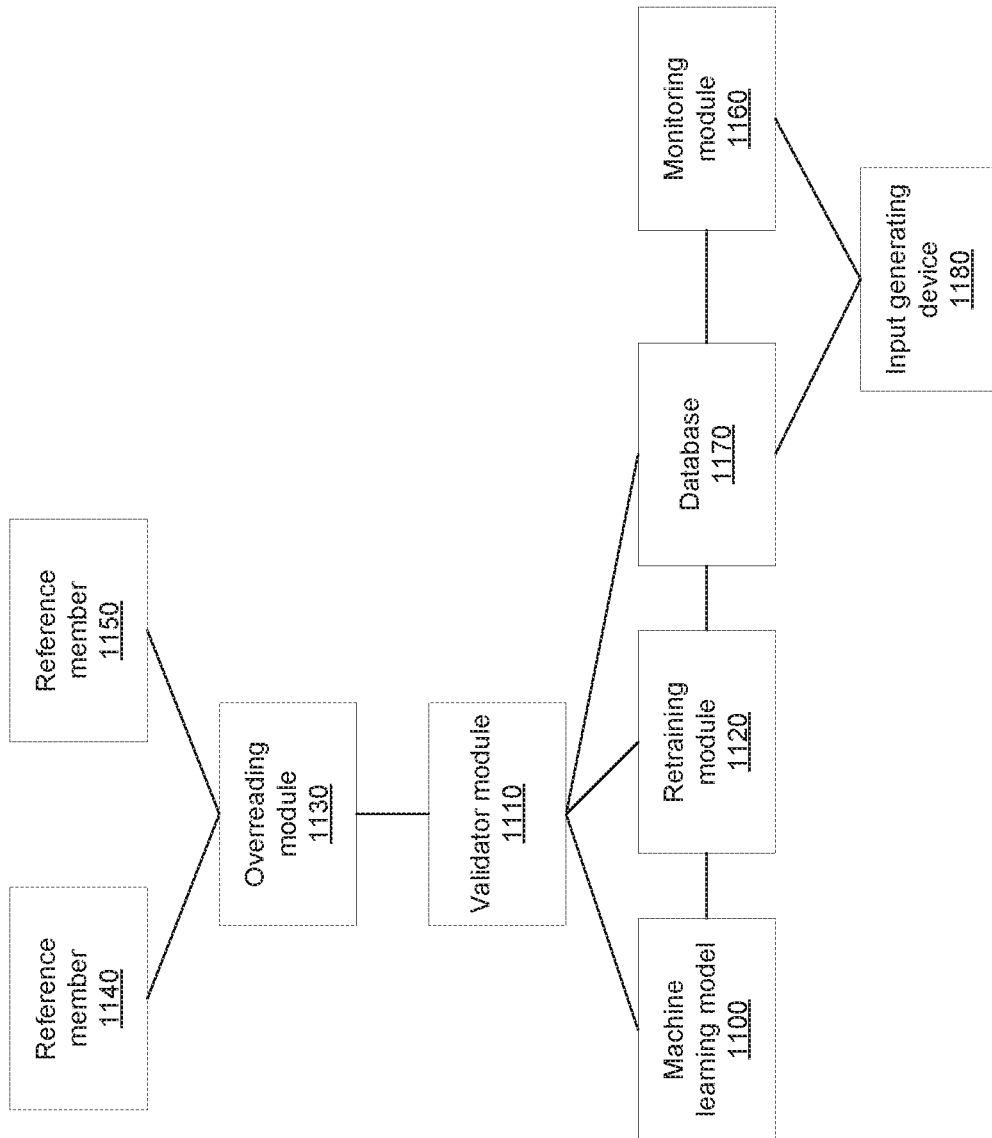
FIG. 11 shows an example system to (1) monitor a performance of a deployed, machine learning model and to (2) detect an anomaly associated with an input.

FIG. 11 shows an example system to perform two phases: phase (1) to monitor a performance of a deployed, machine learning model, and phase (2) to detect an anomaly associated with an input. The performance of the deployed, machine learning model is evaluated based on accuracy of resulting diagnoses. The system includes a machine learning model 1100, a validator module 1110, a retraining module 1120, an overreading module 1130, one or more reference members 1140, 1150, a monitoring module 1160, a database 1170, and a input generating device 1180. The input generating device 1180 can be a microscope, a camera, a transducer, a 3-D scanner, a LIDAR, a keyboard, etc.

The machine learning module 1100 can receive an input such as an image, an audio, text, a 3-dimensional model, etc., and can make an inference based on the input. For example, the machine learning module 1100 can identify a presence of a disease, such as retinopathy, in a medical image.

The validator module 1110 can monitor a performance of a deployed, machine learning model 1100, while the monitoring module 1160 can detect an anomaly associated with the input. To perform phase (1), the validator module 1110 can generate an inference by using the machine learning model 1100 on the input, and can request from multiple reference members 1140, 1150 multiple inferences based on the same input. The reference members 1140, 1150 can be a machine learning model different from the machine learning model 1100, a prior version of the machine learning model 1100, or a professional trained to identify the feature, such as a healthcare professional trained to diagnose a disease. When the multiple inferences are not substantially the same as the inference of the machine learning model 1100, and the multiple inferences are associated with a significant number of inputs sampled, the validator module 1110 can note a decrease in the accuracy of the machine learning model 1100.

For example, the machine learning model 1100 can be given a fundus image, and can produce an inference indicating that an eye of a subject in the fundus image is healthy. The same fundus image can be given to the multiple reference members 1140, 1150. The inference of the multiple reference members 1140, 1150 can indicate that the eye of the subject in the fundus image is diseased. In this case, the multiple inferences are not substantially the same as inference of the machine learning model. Consequently, the validator module 1110 notes the decrease in the accuracy of the machine learning model 1100.

To perform phase (2), the monitoring module 1160 can monitor the actual distribution of inferences over a period of time (with average inference results computed) performed by the machine learning module 1100. The monitoring module 1160 can detect that the anomaly occurred by comparing the latest inference results with the moving average obtained, and report an anomaly if the incoming inference results differ significantly from the moving average.

The validator module 1110 can determine that the decrease in the accuracy of the machine learning model 1100 is a substantial decrease, for example a 10% decrease. When the decrease is substantial, the validator module 1110 can correct the substantial decrease in the accuracy by requesting a retraining of the machine learning model 1100 or by requesting a decommissioning of the machine learning model 1100.

If the decrease in the accuracy exceeds a predetermined value, for example over 20%, then the validator module 1110 can determine to decommission the machine learning model 1100, without an attempt to retrain. Further, the validator module 1110 can estimate an amount of training needed to retrain the machine learning model 1100. If the amount of training needed to retrain the machine learning model 1100 is greater than the amount of time needed to train the machine learning model 1100, the validator module 1110 can decommission the machine learning model 1100, and train a new machine learning model from scratch.

The monitoring module 1160 can record multiple dimensions associated with a process of generating the input. The multiple dimensions include an attribute of the input, an attribute of the input generating device 1180, an attribute of a subject from which the input was generated, etc. The attribute of the input can be a modality of the input, a field of view of the input, an eye position. The attribute of the device generating the input can be a type of camera generating the input. The attribute of the subject from which the input was generated can be a race, a gender, and ethnicity, current health condition, health history, age, location of residence, etc. The database 1170 can store the dimension associated with the process of generating the input as a metadata associated with the input.

The validator module 1110 can compare the performance of the machine learning model 1100 to the reference member 1140, 1150 on a particular dimension. The validator module 1110 can select a dimension such as location of residence of the subject. For example, the location of residence can be a particular county, city, state, country, etc. The validator module 1110 can obtain from the database 1170 multiple inputs in which the subject resides in the selected location, and the multiple diagnoses that the machine learning model 1100 made for the multiple inputs. In addition, the validator module 1110 can obtain multiple diagnoses generated by the reference member 1140, 1150 based on the same multiple inputs in which the subject resides in the selected location. The validator module 1110 can compare the multiple inferences generated by the machine learning model 1100 and the multiple inferences generated by the reference member 1140, 1150 to determine whether there is a substantial difference between the two sets of inferences.

Upon determining that the multiple inferences generated by the machine learning model 1100 substantially differ from the multiple inferences generated by the reference member 1140, 1150, the retraining module 1120 can train the machine learning model 1100 using the multiple inputs of subjects residing in the selected location and the multiple inferences generated by the reference member 1140, 1150.

The overreading module 1130 can ensure that the multiple reference members 1140, 1150 reach consensus before presenting their inferences for comparison with the machine learning model 1100. The overreading module 1130 can request from multiple reference members 1140, 1150 multiple inferences. When the multiple inferences contain a substantial ambiguity, the overreading module 1130 can eliminate the substantial ambiguity by providing the multiple inferences to each reference member 1140, 1150 and requesting set of inferences of inferences, until the substantial ambiguity is eliminated. The substantial ambiguity can be defined as 20% or more of the reference member having the same diagnoses which is different from the diagnoses of the 80% of the remaining reference members.

For example, when there are two reference members, one of the reference members can produce an inference indicating the presence of the disease, while the other reference member can produce an inference indicating an absence of the disease. The overreading module 1130 can supply to each reference member the inference of the other reference member, to have the reference members consider the inference of the other reference member before producing another inference. The process can be repeated until a consensus is reached.

Figure 12:
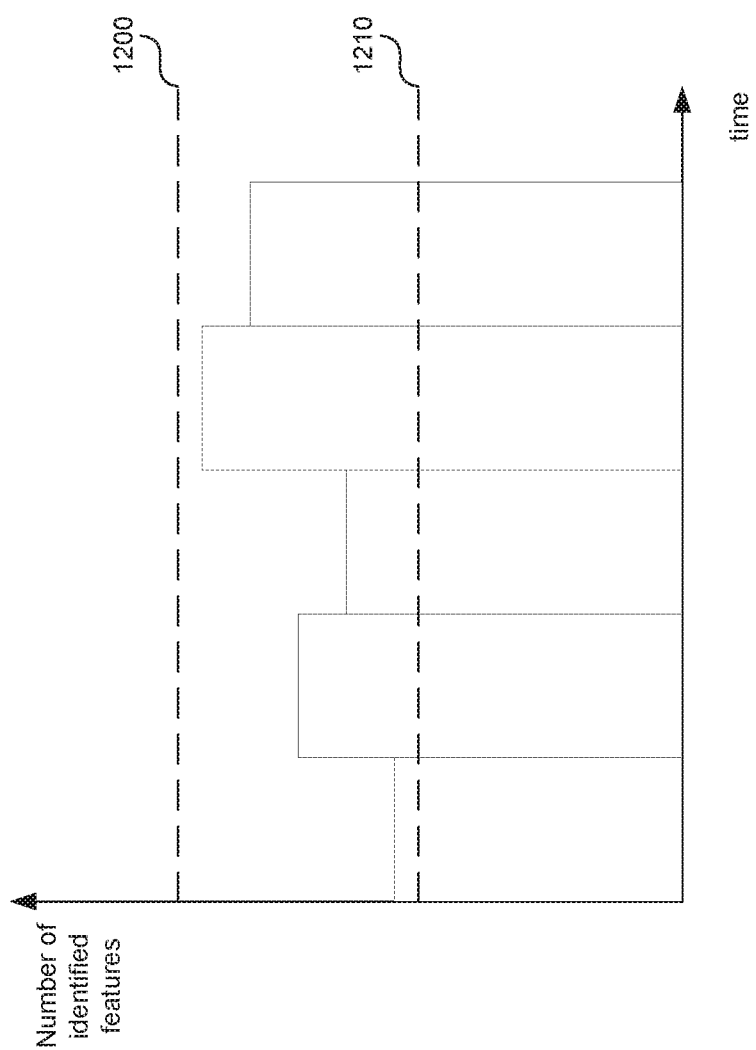
FIG. 12 shows examples of an expected distribution and an actual distribution.

FIG. 12 shows an expected distribution and an actual distribution. The histogram in FIG. 12 shows a number of actual diagnoses made by the machine learning model 1100 in FIG. 11 over a period of time. The period of time can be an hour, a day, a month, etc. The expected distribution, denoted by lines 1200, 1210 shows how many cases of illnesses are expected over the same period of time. The lines 1200, 1210 can be straight, or can be curved. The curved lines indicate that the expected distribution varies with varying time. The expected distribution can be based on the diagnoses made by the machine learning model 1100 over a prior period of time, or the diagnoses made by the reference member 1140, 1150 in FIG. 15. In FIG. 12, the number of actual diagnoses is within the expected distribution range, denoted by lines 1200, 1210.

Figure 13:
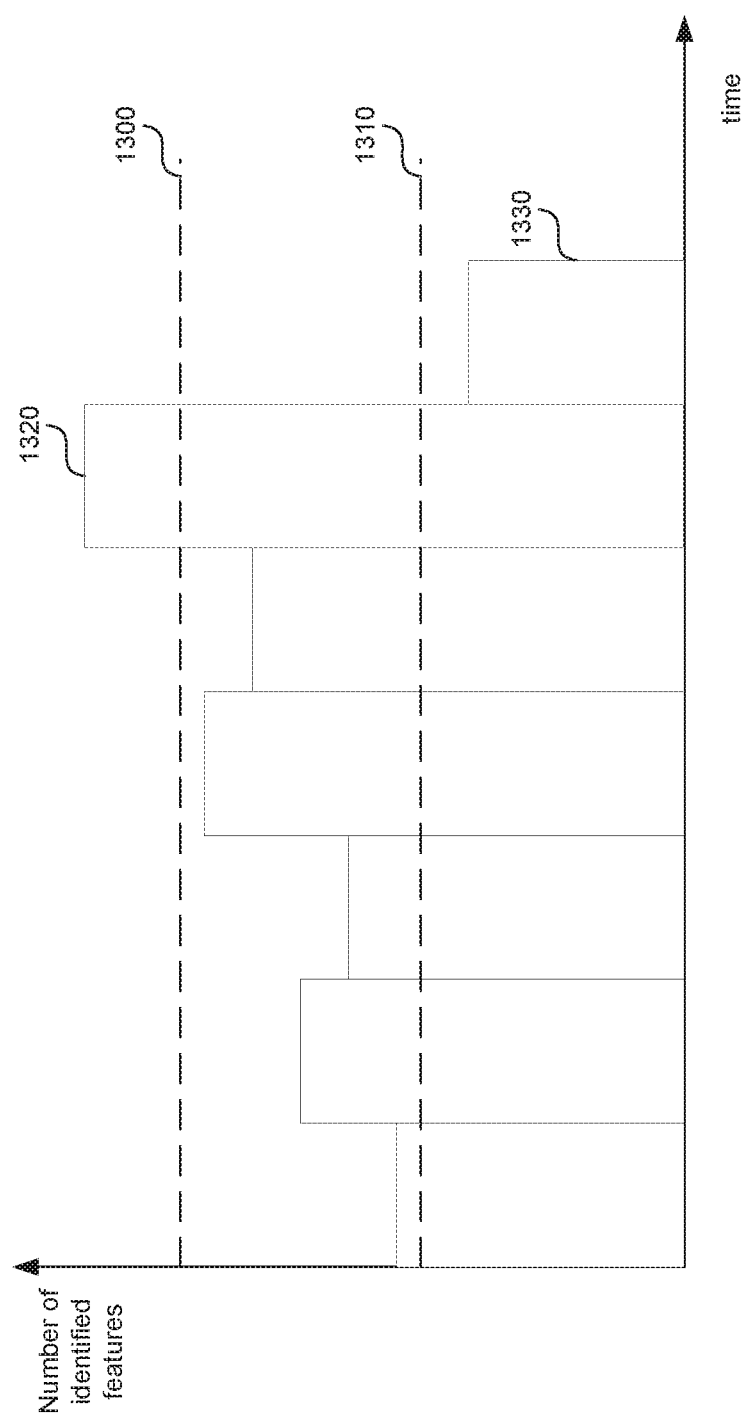
FIG. 13 shows an example anomaly.

FIG. 13 shows an anomaly. The histogram in FIG. 13 shows a number of actual diagnoses made by the machine learning model 1100 in FIG. 11 over a period of time. The histogram in FIG. 13 can also show a percentage of diagnosed illnesses out of all images considered by the machine learning model 1100 over the period of time. The period of time can be an hour, a day, a month, etc. The expected distribution, denoted by lines 1300, 1310 shows how many cases of illnesses are expected over the same period of time. The measurements performed during time periods 1320, 1330 indicate an anomaly because the measurements are above and below the expected number of diagnoses, respectively.

For example, the expected distribution has an expected ratio of diseased versus healthy subjects at 50%:50%+/−10%. However, when the actual distribution has an actual ratio of diseased versus healthy subjects at 10%:90%, the disparity between the actual distribution and expected distribution indicates that further examination of the input and the diagnosis should be performed. The disparity can be explained by a change in process, such as a new camera, a new technician recording the input, a new demographic group of subjects coming into the hospital, or the change can be explained by an error within the machine learning model 1100.

Given that the monitoring module 1160 in FIG. 11 stores the data about the process within the database 1170 in FIG. 11, a temporal correspondence can be established between the change in the process and the disparity in the expected versus actual distribution. For example, if the disparity between the actual and the expected distribution temporally overlaps with the hiring of a new technician, this temporal overlap indicates that the new technician may be taking pictures from a new point of view. Either the technician needs to be retrained, or the machine learning model 1100 needs to be retrained on input images associated with the new point of view.

Figure 14:
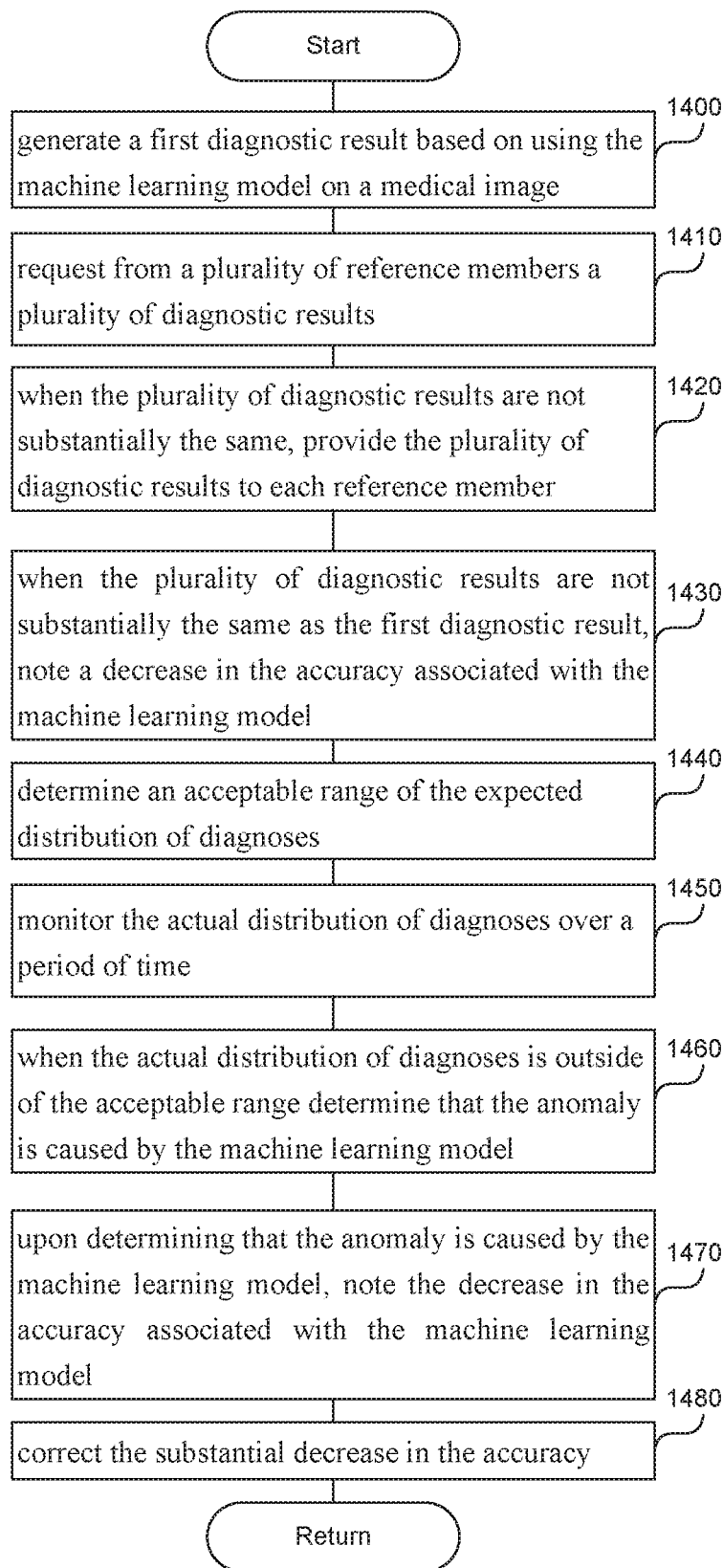
FIG. 14 is a flowchart of a computer-implemented method for (1) monitoring a performance of a deployed machine learning model and (2) detecting anomalies in an input.

FIG. 14 is a flowchart of a computer-implemented method for (1) monitoring a performance of a deployed machine learning model and (2) detecting anomalies in an input. Flowchart steps 1400, 1410, 1420, 1430 are associated with phase (1) above, while flowchart steps 1440, 1450, 1460, 1470 are associated with phase (2) above. Monitoring the performance in post-deployment involves monitoring accuracy of the diagnostic results performed with the machine learning model.

In phase (1), a processor can monitor the quality of a deployed machine learning model by sampling, and over-reading a subset of inputs (i.e., images) received, and can compute metrics to evaluate the model performances and compare them with benchmark metrics.

In phase (2), a processor can detect anomalies from input data by comparing distributions of inference results and other input dimensions (e.g., ethnicity, camera type, technician skill level, etc.) over time with incoming inference results and new input data for a period time. Given multiple images, the machine learning model produces multiple diagnostic results that can create a distribution which varies in a statistically significant way from a distribution generated by the same machine learning model at a different time period. When the difference is sufficiently statistically significant, for example, above a predetermined threshold, the difference can become a performance anomaly.

To perform phase (1) above, a processor, in step 1400, can generate a diagnostic result by using the machine learning model on one or more medical images. The medical image can be a fundus image, an MRI image, an X-ray, an ultrasound, etc. In step 1410, the processor can request from one or more reference members one or more diagnostic results. The reference members receive substantially identical medical image and provide the diagnostic results. For example, multiple ophthalmologists can be consulted for diagnosis of retinal images.

In step 1420, when the multiple diagnostic results are not substantially the same, the processor can attempt to reach consensus among the reference members by providing the diagnostic results to each reference member. In other words, each reference member gets the diagnoses of the others reference members, and can reconsider its diagnosis. After the reference members have had a chance to reconsider their diagnosis, the processor can request a second diagnoses from each reference member, and repeat this process until the reference member diagnoses are substantially the same. For example, if there are ten reference members, substantially the same diagnosis means that at least eight reference members agree. If there are two reference members, substantially the same diagnosis means that both reference members agree. In step 1430, when the multiple diagnostic results are not substantially the same as the first diagnostic result, the processor can a note a decrease in the accuracy associated with the machine learning model.

To perform phase (2) above, the processor, in step 1440 can determine an acceptable range of the expected distribution of diagnoses. In step 1450, the processor can monitor the actual distribution of diagnoses over a period of time. In step 1460, when the actual distribution of diagnoses is outside of the acceptable range the processor can determine that the anomaly is caused by the machine learning model. The processor can make this determination by eliminating a change in the input as a cause of the anomaly. In addition, the processor can send a notification including a discrepancy between the acceptable range and the actual distribution of diagnoses. In step 1470, upon determining that the anomaly is caused by the machine learning model, the processor can note the decrease in the accuracy associated with the machine learning model.

In step 1480, when phases (1) and (2) above indicate a substantial decrease in the accuracy of the machine learning model the processor can correct the substantial decrease in the accuracy by retraining the machine learning model or by decommissioning the machine learning model.

To determine whether the cause of the anomaly is due to a change in the input, or due to inaccuracy of the machine learning model, the processor can monitor a dimension associated with a process generating the medical image to obtain a dimension value. If the anomaly temporally corresponds to the change in a dimension, then, the change in the dimension needs to be investigated first as the likely cause of the anomaly. The dimension can include an attribute associated with the medical image, an attribute associated with a device to generate the medical image, and/or an attribute associated with a subject used to generate the medical image. For example, the attribute associated with the medical image can be stored in the image metadata and can include modality, field of view, eye position, etc. In another example, the attribute associated with the device can include type of camera used to generate the image. In a third example, the attribute associated with the subject can include the subject's age, gender, ethnicity, race, health history, current health condition, etc.

For example, the processor detects at least a 10% change in the actual distribution of diagnoses on Tuesday. On Tuesday, as well, the processor detects a change in the camera metadata indicating that a new type of camera has been installed at the hospital. The 10% anomaly in the actual distribution and the change in the camera metadata temporally correspond to each other. As a result, the processor can send a notification indicating a correlation between the change associated with the dimension and the 10% change in the actual distribution of diagnoses. Likely, the anomaly is not due to the change in the machine learning performance but due to the change in the new camera.

Figure 15:
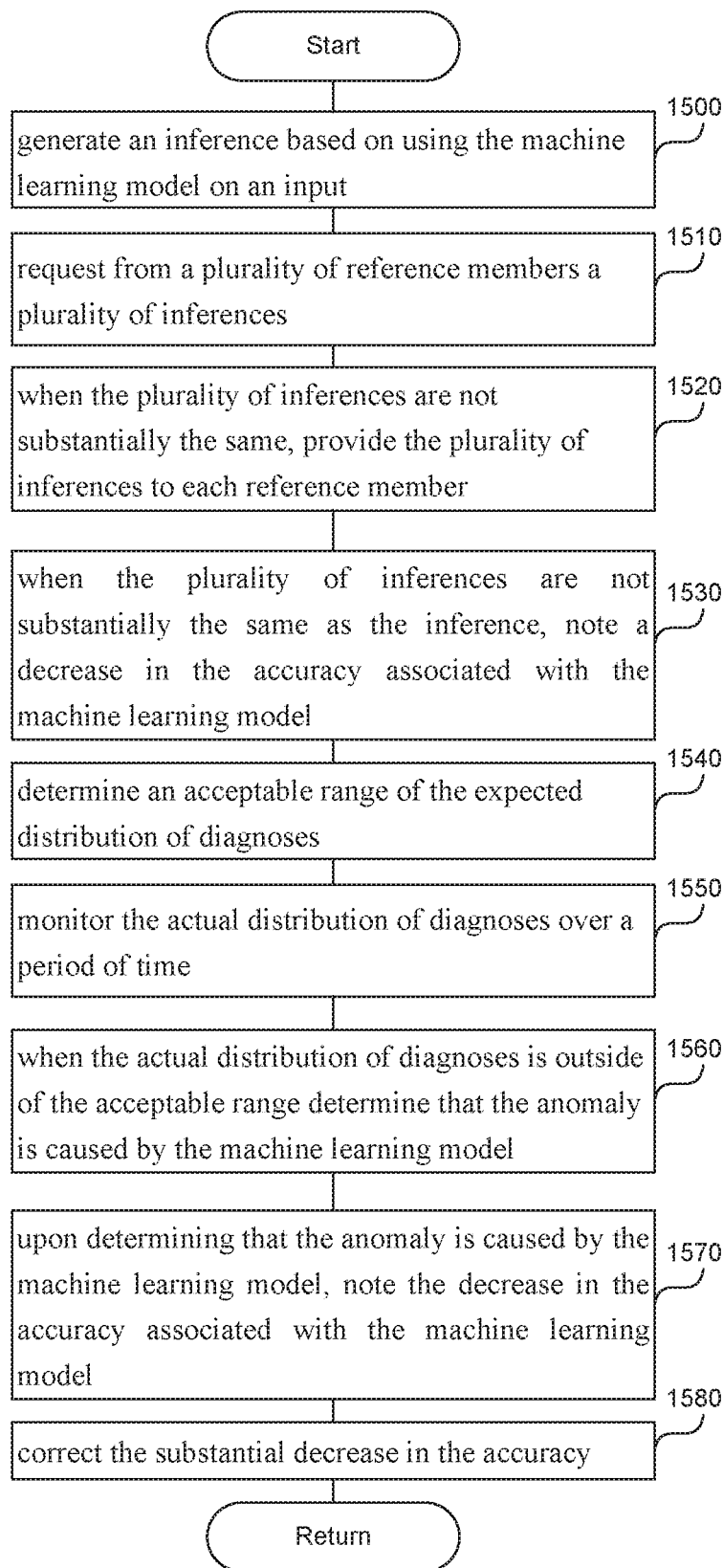
FIG. 15 is another example flowchart of a computer-implemented method for monitoring a performance of a deployed, machine learning model and detecting an anomaly associated with an inference.

FIG. 15 is a flowchart of a computer-implemented method for monitoring a performance of a deployed, machine learning model and detecting an anomaly associated with an inference. To monitor the performance of the deployed, machine learning model, the processor can perform step 1500, 1510, 1520, 1530. To detect the anomaly associated with an inference, the processor can perform steps 1540, 1550, 1560, 1570.

In step 1500, the processor can generate an inference based on using the machine learning model on an input. The input can be an X-ray, an MRI, an ultrasound, a fundus image, an audio, a text, three-dimensional model, etc. In step 1510, the processor can request from one or more reference members one or more inferences. In step 1520, when the multiple inferences are not substantially the same, the processor can provide the inferences of the other reference members to each reference member in an attempt to reach consensus, as described in this application. In step 1530, when each reference member has had an opportunity to consider the inferences of the other reference members, the processor can request another set of inferences, until all the inferences are substantially the same, as described in this application. When the multiple inferences are not substantially the same as the first diagnostic result, the processor can note a decrease in the accuracy associated with the machine learning model.

To detect the anomaly associated with inference, in step 1540 the processor can determine an acceptable range of the expected distribution of inferences, such as ratio of ill to healthy subjects should be 50-50+/−10%. In step 1550, the processor can monitor the actual distribution of inferences over a period of time. In step 1560, when the actual distribution of inferences is outside of the acceptable range the processor can determine that the anomaly is caused by the machine learning model by eliminating a change in the input as a cause of the anomaly. In addition, the processor can send a notification including a discrepancy between the acceptable range and the actual distribution of diagnoses. In step 1570, upon determining that the anomaly is caused by the machine learning model, the processor can note the decrease in the accuracy associated with the machine learning model.

For example, the actual distribution of inferences is 10:90 for the month of August, while the acceptable range of the expected distribution is 50:50+/−10% for the month of August. The processor can detect the anomaly in the distribution and notify a responsible party, or can perform further analysis to determine the root cause of the distribution—specifically, whether the root cause of the distribution is due to the input generating process or due to a problem with the machine learning model.

In step 1580, when monitoring the performance and detecting the anomaly indicate a substantial decrease in the accuracy of the machine learning model, the processor can correct the substantial decrease in the accuracy by retraining the machine learning model or by decommissioning the machine learning model.

To determine the root cause of the distribution anomaly, the processor can monitor a dimension associated with a process generating the input to obtain a dimension value. The dimension can include an attribute associated with the input, an attribute associated with a device to generate the input, or an attribute associated with a subject used to generate the input. The attribute associated with input can be modality, field of view, subject position when the image was taken, ambient noise when an audio is recorded, etc. The attribute associated with the device can be the type of the device used to generate the input, age of the device used to generate the input, last calibration associated with a device, etc. The attribute associated with a subject can be ethnicity, age, sex, race, health history, etc.

The processor can select a first multiple dimension values associated with the dimension and a second multiple dimension values associated with the dimension, so that the first multiple dimension values and the second multiple dimension values correspond to non-overlapping time periods. For example, the dimension can be age of the subjects in the month of July, and the age of the subjects in the month of August. The processor can detect a difference above a predetermined threshold between the first multiple dimension values and the second multiple dimension values. The threshold can be 10% or above. For example, the processor can detect that 10% more elderly subjects have been subjected to the diagnosis process in the month of August than in the month of July. The elderly subjects can be defined as being over 60 years of age. The processor can send a notification to a responsible party including the dimension and the difference. For example, the processor can send an email stating that in the month of August there have been 10% more elderly subjects admitted then in the month of July.

In addition to monitoring age of the subjects, the processor can monitor all the various dimensions collected, and send various alerts. For example, the processor can send an alert if there is a 15% difference between the field of view gathered in the last week, and the field of view gathered in the last two weeks ago. The processor can also send an alert if subject ethnicity differs by 20% from was expected for the last two days. In addition, the processor can send an alert if the camera type differs by 10% from what was expected for the last year.

To determine the root cause of the anomaly, the processor can detect that the anomaly temporally overlaps with a change in the monitor dimension. For example, the processor can determine that in the month of August, there has been a 10% increase in the diagnoses of cancer. In the same time, in the month of August, there has been a 10% increase in admission of elderly subjects. Therefore, the processor can send a notification indicating a correlation between the change associated with the dimension and the anomaly, thereby indicating that the likely cause of the anomaly is the change in the demographic of the subjects. Consequently, the machine learning model can be retrained with an input associated with the selected dimension. For example, the machine learning model can be retrained using fundus images of elderly subjects as input.

In another embodiment, to determine the cause of the anomaly, the processor can determine a time of occurrence of the anomaly, and find a dimension in which a change in the dimension value occurs substantially at the time of occurrence of the anomaly. The processor can send a notification indicating a correlation between the anomaly and the change associated with the dimension.

The processor can compare the performance of the machine learning model to the reference member along a specific dimension, such as comparing the performance of two machine learning models for female subjects. From multiple inputs provided to the machine learning model the processor can select a subset of inputs associated with at least one of an attribute of a subject used to generate the input, an attribute associated with the input, or an attribute associated with a device to generate the input. The attribute can be gender. The processor can compare an inference produced by the machine learning model based on the subset of inputs having women as subjects to an inference produced by the reference member having also women as subjects. The inference can be requested from multiple reference members as described in this application. When the inference of the machine learning model differs from the inference of the reference member, the processor can note the decrease in the accuracy of the machine learning model. The processor can retrain the machine learning model on inputs having women as subjects.

In addition to selecting a specific dimension, an incoming subject record to be sampled for validation can be selected randomly, or can be selected after rigorous statistical analysis. When the record is selected randomly, the challenge/trade-off is that the sample size (i.e. number of inputs) needs to be sufficiently large so that the dimension value drop is significant enough for engineers/researchers to further investigate the root cause, but not too large so too much resources (time & money) are wasted to double check our machine learning model predictions. When the record is selected after rigorous statistical analysis, the rigorous statistical analysis can compute the expected sample size needed, as well as the minimum number of diseased samples needed, to detect various degrees of dimension values drops.

To correct the substantial decrease in the accuracy of the machine learning model, the processor can decommission the machine learning model when a criterion is satisfied. The criterion can include: a substantial decrease in the accuracy compared to a second machine learning model, a substantial decrease in the accuracy compared to the machine learning model at a prior timeframe, or a detection of an anomaly above a predetermined threshold over a predetermined time frame.

Processing System

Figure 16:
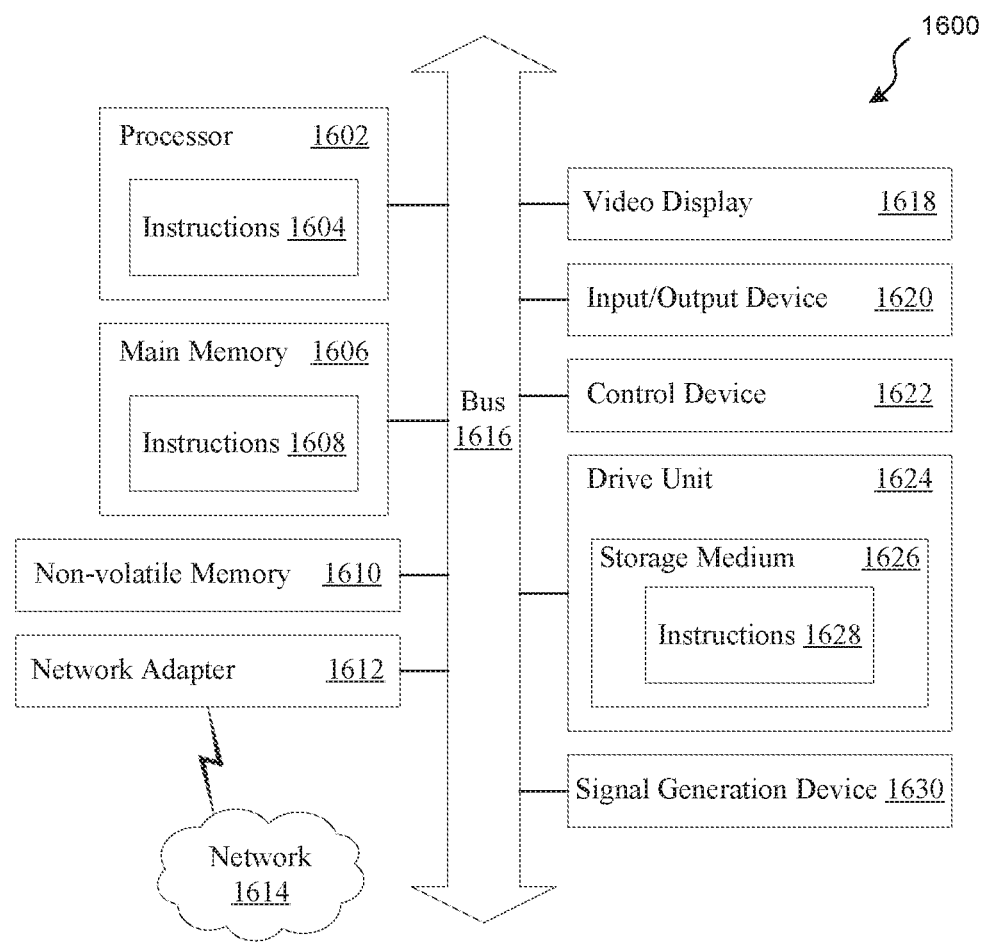
FIG. 16 is a block diagram illustrating an example of a processing system in which at least some operations described herein can be implemented.

FIG. 16 is a block diagram illustrating an example of a processing system 1600 in which at least some operations described herein can be implemented. For example, the machine learning model (e.g., machine learning model 420 in FIG. 4, 1100 in FIG. 11) may be hosted on the processing system 1600. Additionally, the validator module 400 in FIG. 4, 1110 in FIG. 11 may be hosted on the processing system 1600, as well as the training module 410 in FIG. 4 and retraining module 1120 in FIG. 11. The processor as described in this application, can be the processor 1602.

The processing system may include one or more central processing units ("processors") 1602, main memory 1606, non-volatile memory 1610, network adapter 1612 (e.g., network interfaces), video display 1618, input/output devices 1620, control device 1622 (e.g., keyboard and pointing devices), drive unit 1624 including a storage medium 1626, and signal generation device 1630 that are communicatively connected to a bus 1616. The bus 1616 is illustrated as an abstraction that represents one or more physical buses and/or point-to-point connections that are connected by appropriate bridges, adapters, or controllers. The bus 1616, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

In some embodiments the processing system 1600 operates as part of motion capture technology, while in other embodiments the processing system 1600 is connected (wired or wirelessly) to the motion capture technology. The processing system 1600 may operate in the capacity of a server or a client machine in a client-server network environment, or as a peer machine in a peer-to-peer network environment.

The processing system 1600 may be a server, a personal computer, a tablet computer, a personal digital assistant (PDA), a mobile phone, a gaming console, a gaming device, a music player, a wearable electronic device, a network-connected ("smart") device, a virtual/augmented reality system, or any other machine capable of executing a set of instructions (sequential or otherwise) that specify actions to be taken by the processing system 1600.

While the main memory 1606, non-volatile memory 1610, and storage medium 1626 (also called a "machine-readable medium") are shown to be a single medium, the term "machine-readable medium" and "storage medium" should be taken to include a single medium or multiple media (e.g., a centralized or distributed database, and/or associated caches and servers) that store one or more sets of instructions 1628. The term "machine-readable medium" and "storage medium" shall also be taken to include any medium that is capable of storing, encoding, or carrying a set of instructions for execution by the processing system 1600.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1604, 1608, 1628) set at various times in various memory and storage devices in a computing device. When read and executed by the one or more computer processors 1602, the instruction(s) cause the processing system 1600 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1610, floppy and other removable disks, hard disk drives, optical disks (e.g., Compact Disk Read-Only Memory (CD ROMS), Digital Versatile Disks (DVDs)), and transmission-type media such as digital and analog communication links.

The network adapter 1612 enables the processing system 1600 to mediate data in a network 1614 with an entity that is external to the processing system 1600 through any communication protocol supported by the processing system 1600 and the external entity. The network adapter 1612 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1612 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method for evaluating a target machine learning model while the target machine learning model is in use by a medical diagnostic tool, the method comprising:
   monitoring medical diagnostic inferences by the target machine learning model over a period of time;
   determining, based on the monitoring, a number of medical diagnostic inferences by the target machine learning model over the period of time that are indicative of a particular medical condition;
   determining the number of medical diagnostic inferences by the target machine learning model that are indicative of the particular medical condition is outside a specified range, wherein the specified range is based on an expected distribution in the number of medical diagnostic inferences over the period of time;
   detecting a performance anomaly associated with the target machine learning model in response to determining that the number of medical diagnostic inferences by the target machine learning model that are indicative of the particular medical condition is outside the specified range; and
   in response to detecting the performance anomaly:
      causing the target machine learning model to be retrained; or
      causing the target machine learning model to be decommissioned.

2. The method of claim 1, further comprising:
   determining that the performance anomaly is caused by the target machine learning model; and
   decreasing a performance metric associated with the target machine learning model in response to determining that the performance anomaly is caused by the target machine learning model.

3. The method of claim 2, further comprising:
   determining that the performance metric associated with the target machine learning model is below a threshold; and
   in response to determining that the performance metric associated with the target machine learning model is below the threshold:
      causing the target machine learning model to be retrained; or
      causing the target machine learning model to be decommissioned.

4. The method of claim 2, further comprising:
   determining that a decrease in the performance metric associated with the target machine learning model exceeds a threshold; and
   in response to determining that the decrease in the performance metric exceeds the threshold, causing the target machine learning model to be retrained.

5. The method of claim 2, further comprising:
   determining that a decrease in the performance metric associated with the target machine learning model exceeds a threshold; and
   in response to determining that the decrease in the performance metric exceeds the threshold, causing the target machine learning model to be decommissioned without attempting to retrain the target machine learning model.

6. The method of claim 2, further comprising:
   determining that a first decrease in the performance metric associated with the target machine learning model exceeds a first threshold; and
   in response to determining that the first decrease in the performance metric exceeds the first threshold, causing the target machine learning model to be retrained;
   continuing to monitor medical diagnostic inferences by the target machine learning model after the target machine learning model has been retrained;
   determining that a second decrease in the performance metric associated with the target machine learning model exceeds a second threshold; and
   in response to determining that the second decrease in the performance metric exceeds the second threshold, causing the target machine learning model to be decommissioned without attempting to retrain the target machine learning model.

7. The method of claim 2, wherein determining that the performance anomaly is caused by the target machine learning model includes:
   monitoring a dimension associated with a process for generating an input to the target machine learning model; and
   determining that a change in the dimension associated with the process for generating the input does not temporally correspond to the performance anomaly.

8. The method of claim 7, wherein the dimension includes any of: an attribute associated with the input, an attribute associated with a device used to generate the input, and/or an attribute associated with a subject used to generate the input.

9. The method of claim 8,
wherein input is a medical image; and
wherein the attribute associated with the medical image is an image capture context attribute that denotes a modality, a field of view, an eye position, a fundus image metadata, or any combination thereof.

10. The method of claim 8, wherein the attribute associated with the subject comprises an ethnicity designation, an age designation, a gender designation, or a race designation.

11. The method of claim 1, further comprising:
determining that the performance anomaly is not caused by the target machine learning model; and
continuing to use the target machine learning model to generate medical diagnostic inferences in response to determining that the performance anomaly is not causes by the target machine learning model.

12. The method of claim 1, wherein the target machine learning model is configured to process medical images to generate medical diagnostic inferences.

13. The method of claim 1, wherein the specified range varies over time, the method further comprising:
obtaining the specified range for the period of time corresponding to the number of medical diagnostic inferences by the target machine learning model that are indicative of a particular medical condition.

14. The method of claim 1,
wherein determining the number of medical diagnostic inferences by the target machine learning model over the period of time includes determining an actual distribution in the number of medical diagnostic inferences over the period of time; and
wherein the performance anomaly is detected further in response to determining that the actual distribution in the number of medical diagnostic inferences over the period of time is outside the expected distribution in the number of medical diagnostic inferences over the period of time.

15. A system comprising:
a processor; and
a memory coupled to the processor, the memory having instructions stored thereon which, when executed by the processor, cause the system to:
monitor medical diagnostic inferences by a target machine learning model over a period of time;
determine, based on the monitoring, a number of medical diagnostic inferences by the target machine learning model over the period of time that are indicative of a particular medical condition;
determine the number of medical diagnostic inferences by the target machine learning model that are indicative of the particular medical condition is outside a specified range, wherein the specified range is based on an expected distribution in the number of medical diagnostic inferences over the period of time;
detect a performance anomaly associated with the target machine learning model in response to determining that the number of medical diagnostic inferences by the target machine learning model that are indicative of the particular medical condition is outside the specified range; and
in response to detecting the performance anomaly:
cause the target machine learning model to be retrained; or
cause the target machine learning model to be decommissioned.

16. The system of claim 15, wherein determining that the performance anomaly is caused by the target machine learning model includes:
monitoring a dimension associated with a process for generating an input to the target machine learning model; and
determining that a change in the dimension associated with the process for generating the input does not temporally correspond to the performance anomaly.

17. The system of claim 16, wherein the dimension includes any of: an attribute associated with the input, an attribute associated with a device used to generate the input, and/or an attribute associated with a subject used to generate the input.

18. The system of claim 15,
wherein determining the number of medical diagnostic inferences by the target machine learning model over the period of time includes determining an actual distribution in the number of medical diagnostic inferences over the period of time; and
wherein the performance anomaly is detected further in response to determining that the actual distribution in the number of medical diagnostic inferences over the period of time is outside the expected distribution in the number of medical diagnostic inferences over the period of time.

19. A memory having instructions stored thereon which, when executed by a system comprising a processor, are configured to cause the system to:
monitor medical diagnostic inferences by a target machine learning model over a period of time;
determine, based on the monitoring, a number of medical diagnostic inferences by the target machine learning model over the period of time that are indicative of a particular medical condition;
determine the number of medical diagnostic inferences by the target machine learning model that are indicative of the particular medical condition is outside a specified range, wherein the specified range is based on an expected distribution in the number of medical diagnostic inferences over the period of time;
detect a performance anomaly associated with the target machine learning model in response to determining that the number of medical diagnostic inferences by the target machine learning model that are indicative of the particular medical condition is outside the specified range; and
in response to detecting the performance anomaly:
cause the target machine learning model to be retrained; or
cause the target machine learning model to be decommissioned.

20. The memory of claim 19,
wherein determining the number of medical diagnostic inferences by the target machine learning model over the period of time includes determining an actual distribution in the number of medical diagnostic inferences over the period of time; and
wherein the performance anomaly is detected further in response to determining that the actual distribution in the number of medical diagnostic inferences over the period of time is outside the expected distribution in the number of medical diagnostic inferences over the period of time.

* * * * *